United States Patent
Furuya et al.

(10) Patent No.: US 9,872,693 B2
(45) Date of Patent: Jan. 23, 2018

(54) VENOUS VALVE INCISING BLADES, MANUFACTURING METHOD OF THE SAME AND ARTERY REVASCULARIZATION TREATMENT USING THE SAME

(71) Applicants: Takatoshi Furuya, Asahi-shi, Chiba (JP); NUMATA OPTICAL INSTRUMENTS FACTORY, Itabashi-ku, Tokyo (JP)

(72) Inventors: Takatoshi Furuya, Asahi (JP); Kenji Numata, Tokyo (JP)

(73) Assignees: TAKATOSHI FURUYA, Asahi-shi (JP); NUMATA OPTICAL INSTRUMENTS FACTORY, Tokyo (JP)

( * ) Notice: Subject to any disclaimer, the term of this patent is extended or adjusted under 35 U.S.C. 154(b) by 265 days.

(21) Appl. No.: 14/611,963

(22) Filed: Feb. 2, 2015

(65) Prior Publication Data
US 2015/0216548 A1     Aug. 6, 2015

Related U.S. Application Data

(63) Continuation-in-part of application No. PCT/JP2014/052511, filed on Feb. 4, 2014.

(30) Foreign Application Priority Data

Jan. 20, 2015  (JP) .................................. 2015008650

(51) Int. Cl.
*A61B 17/32*  (2006.01)
*A61B 17/3207*  (2006.01)
(Continued)

(52) U.S. Cl.
CPC ................ *A61B 17/320016* (2013.01); *A61B 17/32075* (2013.01); *A61B 2017/00526* (2013.01);
(Continued)

(58) Field of Classification Search
CPC ...... A61B 17/320016; A61B 17/32075; A61B 2017/22097; A61B 17/32053
See application file for complete search history.

(56) References Cited

U.S. PATENT DOCUMENTS

5,047,041 A * 9/1991 Samuels .......... A61B 17/32075
606/159
5,139,506 A * 8/1992 Bush ................ A61B 17/32075
606/159
(Continued)

FOREIGN PATENT DOCUMENTS

DE    3717926 A1    12/1988
JP    H04-122251 A   4/1992
(Continued)

OTHER PUBLICATIONS

"Autologous Reconstruction-INSITUGAT(R) the alterative Atraumatic Vein Valve Cutter for the in situ bypass according to Prof. Gruss, M. D.", Catalogue (St. 02.06.89/1), Woundhealing Division, B. Braun Melsungen AG, Melsungen, Germany (Jan. 1989).

(Continued)

*Primary Examiner* — Alexander Orkin

(57) ABSTRACT

A venous valve incising cutter includes a cutting teeth head, a guide, a wire and a coupling rod that couples the guide and a cutting teeth head, all aligned in a rotation axis thereof. More than four pieces of cutting blades are formed on the outer surrounding surface of the cutting teeth head. Each cutting blade has a roughly triangular pyramid shape such that the three ridge lines are composed of the outer surrounding surface of the cutting teeth head and the two planes formed in the reverse side of the outer surrounding surface and the apex is a knife-point of the cutting blade.

18 Claims, 12 Drawing Sheets

(51) Int. Cl.
  *A61B 17/00* (2006.01)
  *A61B 17/22* (2006.01)
(52) U.S. Cl.
  CPC ............... *A61B 2017/22097* (2013.01); *Y10T 29/49996* (2015.01)

(56) References Cited

U.S. PATENT DOCUMENTS

| | | | |
|---|---|---|---|
| 5,304,189 A | 4/1994 | Goldberg et al. | |
| 5,556,405 A * | 9/1996 | Lary | A61B 17/3207 606/159 |
| 5,601,580 A | 2/1997 | Goldberg et al. | |
| 5,725,543 A * | 3/1998 | Redha | A61B 17/32075 606/159 |
| 5,899,912 A * | 5/1999 | Eaves, III | A61B 17/00008 128/898 |
| 8,491,614 B2 * | 7/2013 | LeMaitre | A61B 17/32072 606/159 |
| 9,333,007 B2 * | 5/2016 | Escudero | A61B 17/32075 |
| 2002/0082614 A1 * | 6/2002 | Logan | A61B 17/11 606/139 |
| 2014/0277037 A1 * | 9/2014 | Grace | A61B 17/32001 606/170 |

FOREIGN PATENT DOCUMENTS

| | | |
|---|---|---|
| JP | 3321165 B2 | 9/2002 |
| WO | 1997/016125 A1 | 5/1997 |

OTHER PUBLICATIONS

Expandable LeMaitre(R)Valvulotome, "Self-Sizing and Self-Centering for More Effective Valvulontomy", Broucher (M0007 Rev. E 06/07) LeMaitre Vascular, Inc., Burlington, Massachusetts, U.S.A. (Jun. 2007).

"Over-the-Wire LaMaitre(R) Valvulotome", Instructions for Use (R2242-01 Rev. H04/14), LeMaitre Vascular, Inc., Massachusetts, U.S.A. (Apr. 2014).

* cited by examiner

C ← → P

Background Art

FIG. 4A
FIG. 4B
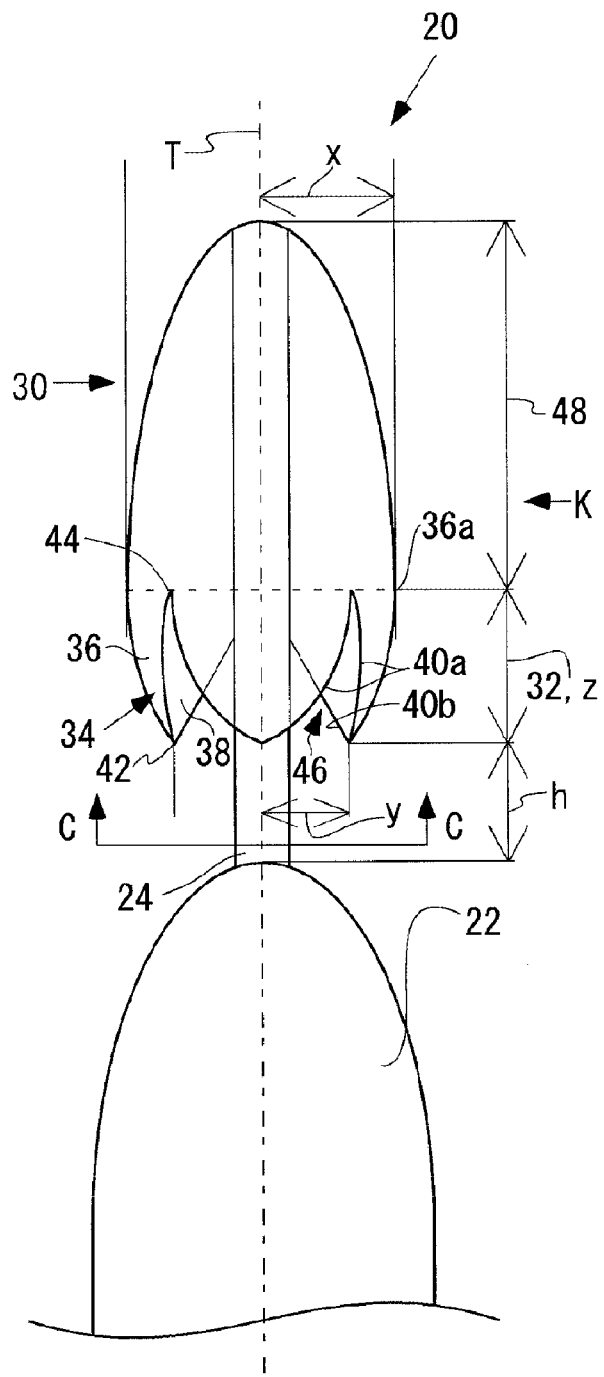
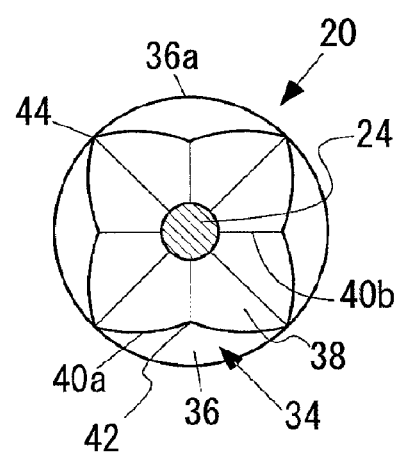

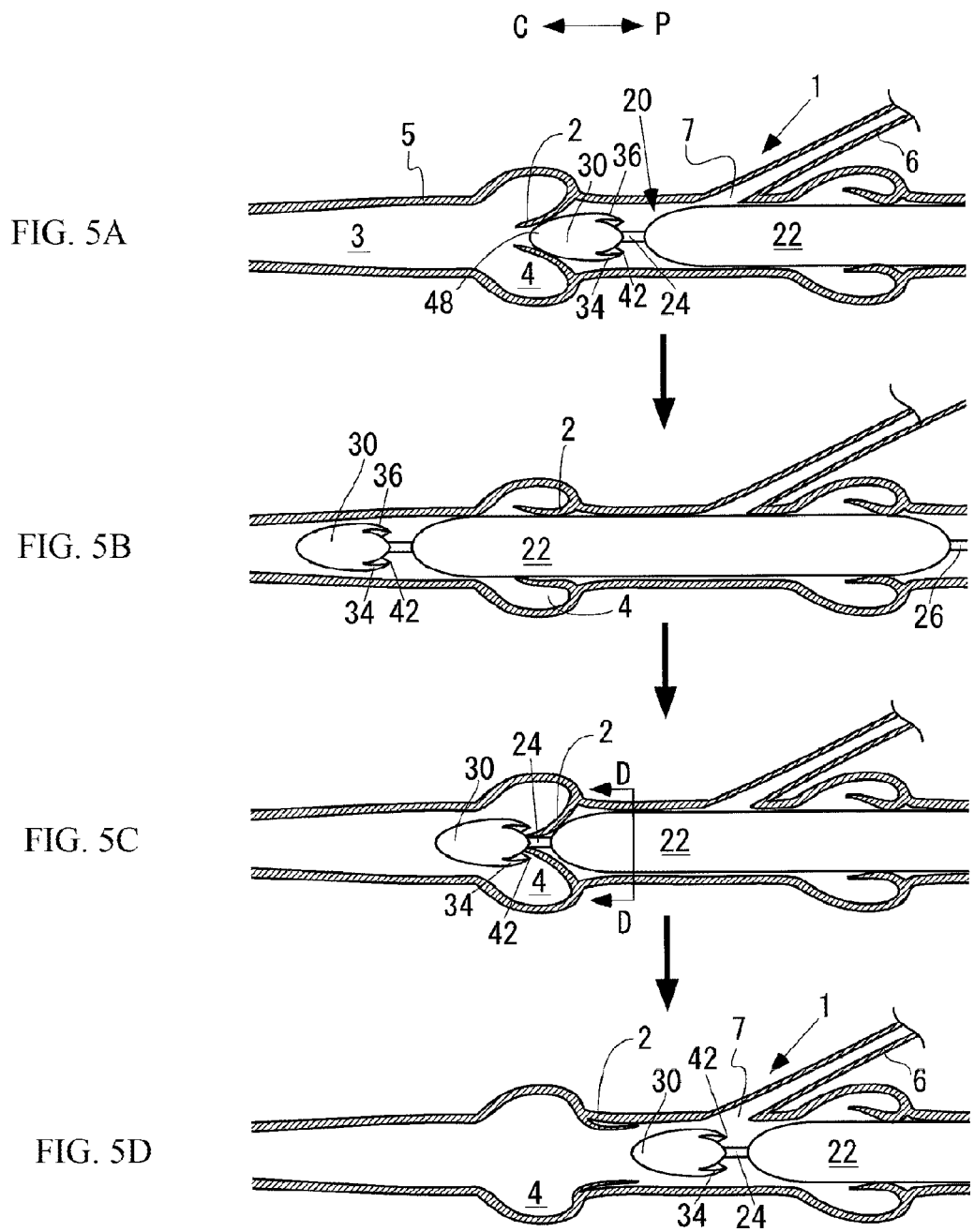

VENOUS VALVE INCISING BLADES, MANUFACTURING METHOD OF THE SAME AND ARTERY REVASCULARIZATION TREATMENT USING THE SAME

TECHNICAL FIELD OF THE INVENTION

The present invention is related to the venous valve incising cutters to cut the venous valves in operations for an autologous vein bypass grafting.

BACKGROUND

Artery occlusion in lower limb due to arteriosclerosis obliterans, Buerger's disease, arterial embolism etc. causes circulatory deficit in legs and toes probably resulting in ulcers and/or necrosis thereof, that is called, severe ischemic limbs. One of reliable therapy for severe ischemic limbs is a bypass surgery to graft an autologous vein to the lower limb artery that has occlusion. An example of such bypass surgery is femoropopliteal artery revascularization.

Patients with arteriosclerosis obliterans recently increase due to aging of population, increase of diabetic patients and dialyzed patients. The increase of patients with severe ischemic limbs that are terminal illnesses of arteriosclerosis obliterans is deeply concerned. However, there is no sufficient number of vascular surgeons that carry out the operation for femoropopliteal artery revascularization.

In femoropopliteal artery revascularization, it is required to bypass the occluded artery from the center (near to heart) to the periphery (far from heart) in order to make blood circulation to periphery over the occluded portion of the artery. For such artery revascularization, a great saphenous vein is autogenously used as the best biomaterial for such bypassing. There are reverse, non-reverse and in-situ treatments for surgical approaches adopted in femoropopliteal artery revascularization.

FIGS. 1A and 1B show blood flow and opening or closing of a venous valve in vein 1. FIGS. 1A and 1B specifically show the opening of a venous valve 2 in the blood flow from the periphery P to the center C and the closing of the venous valve 2 in that from the center C to the periphery P, respectively.

In most cases, arteries exist from the heart to the periphery in parallel to the veins. Arteries have rather thick and elastic blood vessel wall and conduct the artery blood pumped in heartbeat from the heart to the peripheries. On the other hand, vein 1 has less elastic blood vessel wall than artery. The venous blood is pushed back to the heart from the peripheries by opening and closing function of a venous valve 2 and pumping function of muscles in the lower limbs or upper limbs.

The normal venous valve 2 cannot invert opening to the periphery P.

A plurality of venous valves 2 exits in the inner cavity of the vein 1 as shown in FIGS. 1A and 1B. The venous valve 2 is a bileaflet valve and let the blood pass from the peripheries to the center as shown in FIG. 1A. When the blood turns to change the flow orientation as flowing from center to the peripheries, the venous valves 2 close and block such flow orientation of the blood, as shown in FIG. 1B. The center side of the venous valve 2, the intravenous valvular sinus 4 inflates by the blood pressure.

In the reverse treatment, a treatment of those adopted for femoropopliteal artery revascularization, a vein 1 is, as an autologous vein, taken off by cutting it off from a vein staying usually near body surface. Putting it in the center C side in the periphery side, the cut end of the center side of the vein is anastomosed to the periphery side of the occluded portion of the artery and then the cut end of the periphery side of the vein to the center side of the occluded portion of the artery.

In the non-reverse treatment, the vein is not reversely put, as the center C side is put in the periphery side after cutting off and it is anastomosed to the artery over the occluded portion as the center side of the vein is anastomosed to the center side of the occluded portion of the artery and the periphery side to the periphery side of the occluded portion of the artery. The orientation of the harvested vein is same as that of the artery.

In the in-situ treatment, the vein existing close to and in parallel to the artery that has an occlusion is anastomosed thereto as a bypassing blood vessel.

In-situ treatment is superior to the reverse treatment and the non-reverse one in terms of not cutting off from the vein to obtain the grafting vessel. In the actual treatment, the vein close to the artery is cut at the center side and periphery side parallel to those sides of the occluded portion of the artery. The vein is harvested from the original position of the cut portion of the vein 1. The branching vessel 6 that branches from the harvested vein is closed and the harvested vein is anastomosed to the artery at the two cut ends but still staying in parallel to the artery.

In the reverse treatment, the orientation of blood flow in the vessel is unchanged before and after grafting since the vein 1 as cut as an autologous vein 1 (as shown in FIGS. 1A and 1B) is reversely put the center C side to the periphery side. Therefore, the artery blood does not stagnate in the vessel after anastomosing the vein to the artery without cutting venous valves.

However, the veins tend to be generally thicker as closer they are to the heart. Even in case that they have the same diameters in the center C side and the peripheries P side, the portion in the center C has more elastic and stretchable than that in the peripheries P. Therefore, the harvested vein has to be anastomosed to a thick artery in the center C side with the periphery side of the thin portion of the harvested vein and thin artery in the periphery P side with the center side of the thick portion of the harvested vein.

On the other hand, the thick and elastic portion of the vein 1 (that is, the center C side of the vein 1) can be anastomosed to the thick portion of the artery and the thin and less elastic portion of the vein 1 (that is, the periphery P side of vein 1) to the thin portion of the artery in the non-reverse and the in-situ treatments. As the result, the anastomosed vein has the similar taper by nature to the artery as the thicker the closer to the heart.

However the artery blood flow, that is in the orientation from the center C side to the peripheries P, is inverse flow orientation in the vein 1 (an autologous vein). Therefore, the blood flow in the grafted vein (an autologous vein) anastomosed to the artery is blocked by the venous valves 2. To obtain normal blood flow of the grafted vein in non-reverse and in-situ treatments, a treatment to destroy the venous valves 2 in the vein 1 (an autologous vein) is required.

BACKGROUND ART

Medical tools to destroy the venous valves 2 are disclosed as prior arts in the Patent Document and two Non-Patent Documents enlisted bellow.

FIGS. 2A to 2E are explanatory drawings of a conventional venous valve incising cutter 10 disclosed in the Patent Document 1 and the Non-Patented Document 1. FIG. 2A shows an overall view of the conventional venous valve incising cutter 10. FIG. 2B shows a zoom-in view of "H" of the conventional venous valve incising cutters 10 inserted in the vein 1. FIG. 2C is a fragmentary view taken in the direction of the arrows "A" of FIG. 2B. FIG. 2D shows a zoom-in view of "H" of the conventional venous incising blade 10 which is rotated in 90 degrees and inserted into the vein 1. FIG. 2E shows a fragmentary view taken in the direction of the arrows "B" of FIG. 2D.

For the purpose of ease of explanation, the second rod 12 is not depicted in FIGS. 2C and 2E. The black small circles represent the apex positions of the cutting blades 15a.

The conventional venous valve incising cutters 10 as disclosed by the Patent Document 1 and the Non-Patented Document 1 include a first rod 15 of which whole shape fits to the venous valvular sinus 4, a second rod 12 that has the same diameter as the first rod. The conventional venous valve incising cutters 10 also includes a link rod 14 that makes linage between the first rod and the second rod and a flexible wire 16. The first rod 15 and the second rod 12 are made of a plastic.

The first rod 15 has a cylindrical body and a rounded-tipped cone at the front half. The cylindrical body has backwardly a circular truncated cone shape or a slightly taper shape and the terminal end thereof is cut in a V-formation at the center axis. The terminal edge is formed into a non-sharp tip incising blade 15a. The Patent Document 1 discloses that the overall shape of the first rod 15 is formed into a shape fitting to the venous valvular sinus 4 and the Non-patent Document 1 that the first rod 15 is formed into a reversely oriented shape of the venous valvular sinus 4.

The second rod 12 has a rounded front end, a cylindrical shape body and a cone shape rear end.

The venous valve cutter disclosed by the Non-patented Document 2 has four thin metal strips around the axial rod. The strips are curved outwardly and have partly cutting blades along thereof. A wire is connected to the end of the axial rod. In order to the inner diameters of the vessels, the diameter of the cutting blades is adjusted by surgeons.

However, the conventional venous valve incising cutter 10 disclosed by the Patent Document 1 and the Non-patented Document 1 has the following problems and does not satisfy the purpose such that surgeons can safely, surely cut the venous valves in a short time.

Example of the venous valve incising cutters and relevant arts are found in, for example, the following documents, all of which are incorporated by reference.

Patent Document 1: Japanese Patent Application Publication No. 1992-122251

Non-Patent Document 1: "Autologous Reconstruction-IN-SITUGAT® the alterative Atraumatic Vein Valve Cutter for the in situ bypass according to Prof. Gruss, M. D.", Catalogue (St. 02.06.89/1), Woundhealing Division, B. Braun Melsungen AG, Melsungen, Germany (January, 1989)

Non-Patent Document 2: Expandable LeMaitre® Valvulotome, "Self-Sizing and Self-Centering for More Effective Valvulontomy", Broucher (M0007 Rev. E 06/07) LeMaitre Vascular, Inc., Burlington, Mass., U.S.A. (June, 2007)

Non-Patent Document 3: "Over-the-Wire LeMaitre® Valvulotome", Instructions for Use (R2242-01 Rev. H04/14), LeMaitre Vascular, Inc., Massachusetts, U.S.A. (April, 2014)

Any discussion of problems and solutions involved in the "background art" has been included in this disclosure solely for the purposes of providing a context for the present invention, and should not be taken as an admission that any or all of the discussion were known at the time the invention was made.

BRIEF SUMMARY OF THE INVENTION

Problems to be Solved

Problems that the conventional venous valve incising cutter 10 disclosed by the Patent Document 1 and the Non-patented Document 1 has are discussed in the following paragraphs.

The first rod 15 has a straight cylindrical shape that has no taper in the center body. The terminal end is cut in a V-formation at the center axis and it is formed to fit to the inner shape of the venous valvular sinus 4. Therefore, each cutting blade 15a of the conventional venous valve incising cutters 10 corresponds to each leaf of the venous valve 2. The V-formation provides a non-blade portion or an empty space between two cutting blades 15a. Since the first rod 15 has a cut-off shape with the V-formation at the center axis of the cylindrical shape, a side view of the cutting blade 15a (FIG. 2B) is different from the other side view of the cutting blade 15a with 90 degrees rotation along the axis of a link rod 14. The first view shows a straight profile at the end portion (FIG. 2B) and the second view a tapered end (FIG. 2D) cone. In a sense of 3D, the end of the first rod 15 has a flat wedge shape that has gradually thinning to the end.

Since the vein 1 divaricates to many rami 6 (see FIGS. 1A and 1B), an intensive care not to cleave the vein 1 by sticking to rami 6 with the conventional venous valve incising cutters 10 is required in the treatment of destroying the venous valve 2 of the vein 1 (an autologous vein).

However the conventional venous valve incising cutters 10 disclosed in the Patent Document 1 and the non-patented document 1 have a flat wedge shape that has gradually thinning to the end and the V-formation at the end thereof provides the non-blade portion or the empty space between two cutting blades 15a, a vessel wall 5 tends to come to the space between the first rod 15 and the second rod 12. In the plane that includes the apex of the two cutting blades 15a, the cutting blades are formed slightly in an inner side to the outer profile of the first rod 15. In another plane that is vertical to this plane, each apex of the two cutting blades 15a is close to the outer profile of the first rod 15.

Due to this physical shape, the vascular tissue such as a rami 6 tends to come close to the apex of the cutting blade 15a and the cutting blade 15a may hook the rami 6

Since the cutting blades 15a of the conventional venous valve incising cutters 10 have a non-sharp tip shape, the apex of the cutting blades 15a hook the venous valves 2 and destroy the venous valves 2 by non-sharply tearing them in a pulling action of a flexible wire 16 attached to the conventional venous valve incising cutters 10. Therefore, the debrided surface of the venous valves 2 is rough surface.

When the two cutting blades 15a locate in the gap of the bileaflet valves of the venous valve, the cutting blades 15a slip out the venous valve since the conventional venous valve incising cutter 10 has a flat wedge shape that has gradually thinning to the end (see FIG. 2D and FIG. 2E). Therefore, the conventional venous valve incising cutter 10 cannot destroy the venous valves 2 unless the two cutting blades 15a locate in such an arrangement that the plane including the apex of the two cutting blades 15a is vertical to the fringes of the venous valves 2 (see FIG. 2B and FIG. 2C and come to the closed state of the venous valves 2. The closed state of the venous implies that the venous valves 2 come to the space between the first rod 15 and the second rod 12.

In order to surely destroy the venous valves 2 by using the venous valve incising cutter 10, the multiple treatment process such as inserting into and drawing out from the vein 1 for each 45 degrees to 90 degrees angle rotation of the conventional venous valve incising cutter 10 against the vein 1 is required. Therefore the vascular surgeons need long time for the treatment and there is a concerning that the treatment may damage the vessel endothelium.

Since the blade disclosed in the Non-Patent Document 2 a sharply spires at the forefront and is toward to the external side of the blade, there is a risk such that the blade is stuck against vascular bifurcation 6 and tears the vein 1. Non-Patent Document 3 discloses cutting blades of which outward expansion is limited by the internal diameter of the vein, however it has such a constraint regarding the rotational angle in the vein that the cutting blades and the centering hoops have to have the right angle to an opening/closing direction of the venous valve.

There have been risks that the conventional venous valve incising cutters 10 and the venous, both having been conventionally used, are stuck against vascular bifurcations 6. Though there is a merit that the vessel wall 5 of the grafted vein in the non-reverse and in-situ treatments has the similar taper by nature to the artery and further merit that patients receive less physical strain from the treatment and the less-invasiveness of the treatment especially in case of in-situ treatment, these treatments are not popular or widely adopted and only executed with LeMairtre's venous vein cutter.

The present invention provides a solution to solve the problems described above. In other words, the purpose of the present invention is to provide a venous valve incising cutter, manufacturing method thereof and artery revascularization treatment method using the venous valve incising cutter by which even less-experienced surgeons can safely and easily incise the venous valves without damaging the vessel endothelium and the vascular bifurcation by reciprocating insertion of the venous valve incising cutter.

Means of Solving the Problems

The present invention provides a venous valve incising cutter, that includes a cutting teeth head having a fore portion having partly spheroid shaped and a posterior portion coupled to a guide, has cutting blades formed around the outer surrounding surface of the posterior portion of the cutting teeth head, of which the cutting blades are partly composed of the outer surrounding surface thereof and have knife-points or non-sharp tip toward the guide. Since the cutting blades conform with the outer surrounding surface of the cutting teeth head, the cutting blades can hit the venous valves, whichever rotational angle vascular surgeons insert the venous valve incising blade regarding the present invention to the vein with, it is possible to cut the venous valves in a one-action treatment, that is, inserting the a venous valve incising cutter into the vein and pulling it out therefrom. The feature of this one-action treatment is from the effect that the cutting blade can hit the venous valves in any rotational angle in the vein since the cutting blades of the a venous valve incising cutter are formed around the outer surrounding surface of the cutting teeth head, of which the cutting blades are partly composed of the outer surrounding surface of the cutting teeth head that has solid revolution geometry.

As for the above effect such that the cutting blade can hit the venous valves in any rotational angle in the vein, the present invention provides another concrete construction, that is, more than four pieces of the cutting blades formed on the outer surrounding surface of the cutting teeth head are arranged on the outer surrounding surface of the posterior portion of the cutting teeth head that has a solid revolution geometry and each piece of the cutting blades has s roughly triangular pyramid shape such that the apex is the knife-point of the cutting blade, one of three pyramid surfaces the outer surrounding surface of the posterior portion of the cutting teeth head and the remaining two pyramid surfaces the two plains formed in the reverse side of the outer surrounding surface. The cutting blades have three roughly triangular pyramids that have three ridge lines composed of the outer surrounding surface of the cutting teeth head and the two planes formed in the reverse side of the outer surrounding surface.

In order to provide the effect that the venous valve incising cutter regarding the present invention easily moves in the vein and does not damage the vessel wall, the fore portion of the cutting teeth head has a hemispheroid shape and the major radius is larger than the maximum radius of the cutting teeth head and the posterior portion has a shape of a hemispheroid of which major radius is smaller than the major radius of the hemispheroid of the fore portion or a shape of a hemisphere of which radius equals to that of the maximum radius of the cutting teeth head or the cutting teeth head partly has an egg-shape revolution as a whole.

As another shape that the venous valve incising cutter enables to easily move in the vein and hardly damage the vessel wall and the cutting blades hit the venous valves in any rotational angle in the vein and do not damage the vessel walls, the venous valve incising cutter regarding the present invention includes a guide that has a shape of a hemispheroid in the fore portion and the posterior portion and cylinder in the middle portion all aligned in the same rotational axis, a coupling rod that extends from the fore portion of the guide and has a radius smaller than that of the cylinder shape of the guide, a cutting teeth head coupled with the coupling rod both aligned in the same rotation axis and a flexible wire connected to the guide within the same rotation axis at the reverse side to the coupling rod, where the cutting teeth head has a shape that a posterior portion is narrow down to the end and the maximum diameter of the cutting teeth head is larger than that of the coupling rod and the posterior portion has more than four pieces of the cutting blades formed on the outer surrounding surface of the cutting teeth head and arranged on the outer surrounding surface of the posterior portion of the cutting teeth head, each piece of the cutting blades having a roughly triangular pyramid shape such that the apex is the knife-point of the cutting blade, one of three pyramid surfaces is a part of the outer surrounding surface of the posterior portion thereof and the remaining two pyramid surfaces have a ridge line being toward the rotational axis. The remaining two planes may be formed in the reverse side of the outer surrounding surface of the posterior portion of the cutting teeth head.

As the shape that enables the venous valve incising cutter to easily move in veins, the cutting teeth head has a shape of hemispheroid both in the fore portion and the posterior portion of which major radius is smaller than that of the fore portion or that has a shape of a hemisphere or a shape of an egg-shape revolution as a whole.

The cutting edge has a knife-point which is in the inner range of the maximum rotational surface radius of the cutting teeth head. However, the cutting edge may have a non-sharp tip or round shape at the fore edge.

The two ridge lines of each cutting blade, which are the edges made in the outer surrounding surface of the cutting teeth head, form curved lines like as the sides of Reuleaux triangle.

The ridge lines of all of the cutting blades continuously surround the outer surrounding surface of the cutting teeth head in a series.

The two facing ridges of adjacent cutting blades have a common end point in a circle of the maximum radius of the cutting teeth head.

Providing the maximum radius of the cutting teeth head be x, the distance between the knife-point of the cutting blade and the rotational axis y, the distance between the knife-point of the cutting blade and the front end of the guide h and assuming an arc of the posterior portion of the cutting teeth head in a plane including the rotational axis have a length z along the axial direction, y/x is in the range of 1/3 to 1/2, z/2x in that of 0.8 to 1.3 and x/h more than equal to 1.3, where there is no upper limit in z/2x since the venous valves 2 can thrust into the gap or the separation length between the cutting teeth head 30 and the guide 22.

As the composition that the venous valve incising cutter regarding the present invention easily moves in the vein, the guide of the venous valve incising cutter includes a main guide and one or more sub-guides all coupled with coupling rods in series.

As another concrete composition of the venous valve incising cutter with that even junior vascular surgeons can safely and easily incise the venous valves in an one-action treatment as insertion and evulsion, the present invention provides a venous valve incising cutter that has a coupling rod enabling to extend the gap or the separation length between the cutting teeth head and the guide, instead of the coupling rod that has a fixed length therebetween as previously explained. To realize the extendibility of the gap or the separation length, the present invention further provides a venous valve incising cutter that has an extendable coupling rod comprising a variable length rod that can change the gap or the separation length between the cutting teeth head and the guide and a coil spring that is fixed to the cutting teeth head and the guide and includes the variable length rod in the inside of the coil.

The present invention also provides a manufacturing method that is characterized by a plurality of processes to cut out the posterior portion of the cutting teeth head around the about rotational axis with a cutting angle against the rotational axis to form the above cutting blades that has a shape of a roughly triangular pyramid. For example, for the cutting teeth head that has four cutting blades of rough triangular pyramid shape, a cutting process is carried out to slit the posterior portion of the cutting teeth head up in a plane at a certain inclined angle (non-vertical angle) to the rotational axis toward the diameter of the posterior portion. This process is carried out in every 90 degrees rotation in all around (that is 360 degrees) the rotational axis. The two processes in 180 degrees difference make a V-shaped cutout in the posterior portion of the cutting teeth head, and the other two processes in 180 degrees difference make the other V-shaped cutout. This cutout has 90 degrees rotation angle against that cutout. These V-shaped cutout form two planer surfaces of the roughly triangular pyramid for each of the four cutting blades. The two planar surfaces and the outer surrounding surface of the cutting teeth head which is the third surface thereof, form the roughly triangular pyramid. When uncut remnants remain in the central part around the rotational axial, the remnants can be removed by drilling such central part of the cutting teeth head.

For the cutting teeth head that has more than four and even number pieces of cutting blades, the cutting process is preferably carried out to every angle that is the angle of 360 degrees divided by the number of the cutting blades, in all around the rotational angle.

For the cutting teeth head that has an odd number of pieces of cutting blades, the following manufacturing method is preferably taken. The manufacturing method is characterized by a first cutting process is carried out to slit the posterior portion of the cutting teeth head up in a plane at a certain inclined angle (non-vertical angle) to the rotational axis toward the radius (that is, from the outer surrounding surface of the posterior portion up to the rotational axis) of the posterior portion. This process is carried out in every angle, that is, the angle of 360 degrees divided by the number of the cutting blades. In this series of the processes, a plane of the roughly triangular pyramid is formed for all of the cutting blades. The other plane of two planes of the roughly triangular pyramid is formed by a cutting process to slit the posterior portion of the cutting teeth head up in a plane including the point to be the knife-pint of the cutting blade at the symmetrically same inclined angle to the rotational axis toward the radius (that is, from the outer surrounding surface of the posterior portion up to the rotational axis) of the posterior portion. This cutting process is carried out to the same every angle as the first process in all around the rotational angle. When uncut remnants remain in the central part around the rotational axial, the remnants can be removed by drilling such central part of the cutting teeth head. Of cause, this manufacturing method may be applied to the cutting teeth head that has an odd number of pieces of cutting blades.

For these manufacturing methods, the cutting surfaces or burr on the edges as cut is preferably removed by drilling or milling and these surfaces or edges are further preferably ground or polished if necessary.

Effects of the Present Invention

The venous valve incising cutter regarding the present invention has a characteristic effect that vascular surgeons can handle the cutting blades hitting to the venous valves, whichever rotational angle the surgeons insert the venous valve incising cutter to the vein with, since the cutting teeth head partly spheroidally-formed in the fore portion and a posterior portion coupled to a guide, has cutting blades formed around the outer surrounding surface of the posterior portion of the cutting teeth head, of which cutting blades are partly composed of the outer surrounding surface of the posterior portion thereof and have knife-points toward the guide, therefore a one-action treatment as insertion and evulsion of the venous valve incising cutter against the vein is possible to incise the venous valves.

The present invention has further effect that vascular surgeons can handle the cutting blades hitting to the venous valves, whichever rotational angle the surgeons insert the venous valve incising cutter to veins with since the cutting teeth head has more than four cutting blades surrounding the surface of a revolution shaped body though the venous valves has a form of a bileaflet valve, therefore a one-action treatment as insertion and evulsion of the venous valve incising cutter against veins is possible to incise the venous valves.

The present invention has further effect that the shape of the cutting blades, that is especially the outer surrounding surface 36 of the cutting stabber 34, block the vessel endothelium and the vascular bifurcation come close the knife-points of the cutting blades, therefore the vascular surgeons who have less experiences of non-reverse and in-situ treatments in artery revascularization treatment can safely and easily incise the venous valves without damaging the vessel endothelium and the vascular bifurcation by reciprocating insertion so that a safe artery revascularization treatment is ensured.

The present invention has further effect that the venous valve incising cutter can incise the venous valves with smooth incised surfaces since each cutting blade has three sharp ridges and a knife-point.

The present invention has further effect that the venous valve incising cutter can smoothly move inside of the veins and surgeons can safely and easily incise the venous valves without damaging the vessel endothelium and the vascular bifurcation by reciprocating insertion since the coupling rod that couples the cutting teeth head and the guide is extendable to change the gap or the separation length therebetween.

The present invention provides a manufacturing method that enables to form cutting blades in the posterior portion of the cutting teeth head.

The present invention contributes to increase the population of vascular surgeons who can operate artery revascularization treatment since the venous valve incising cutters regarding the present invention does not require many experiences and long term training for the surgeons. Those result in saving many patients form serious circulatory diseases such as ischemia-induced necrotic limbs, leg amputation etc.

BRIEF DESCRIPTION OF THE DRAWINGS

FIG. 1A is a schematic of the venous valve 2 opening in the blood flow, and FIG. 1B is a schematic of the venous valve 2 closing in the blood flow.

FIGS. 2A to 2E are explanatory drawings of a conventional venous valve incising cutter 10 functioning at a venous valve in a vein 1.

FIGS. 4A and 4B schematically illustrate the venous valve incising cutter regarding the first embodiment. That is, FIG. 4A is a schematic of a zoom-in view of the part surrounded with the rectangular J, and FIG. 4B is a schematic viewing from C-C in FIG. 4A.

FIGS. 5A to 5D schematically illustrate the use of the venous valve incising cutter regarding the first embodiment. That is, FIGS. 5A to 5D are schematics explaining progressive steps in using the venous valve incising cutter.

FIGS. 6A to 6D are schematics explaining the function of the venous valve incising cutter regarding the first embodiment.

FIG. 11A is a zoom-in view of the front part, and FIG. 11B is a schematic viewing from E-E in FIG. 11A.

FIG. 12A is a schematic illustrating a short gap between the cutting teeth head and the guide, and FIG. 12B is a schematic illustrating the expanded gap between the cutting teeth head and the guide so that the venous valve thrusts into the gap.

Figure 1A:
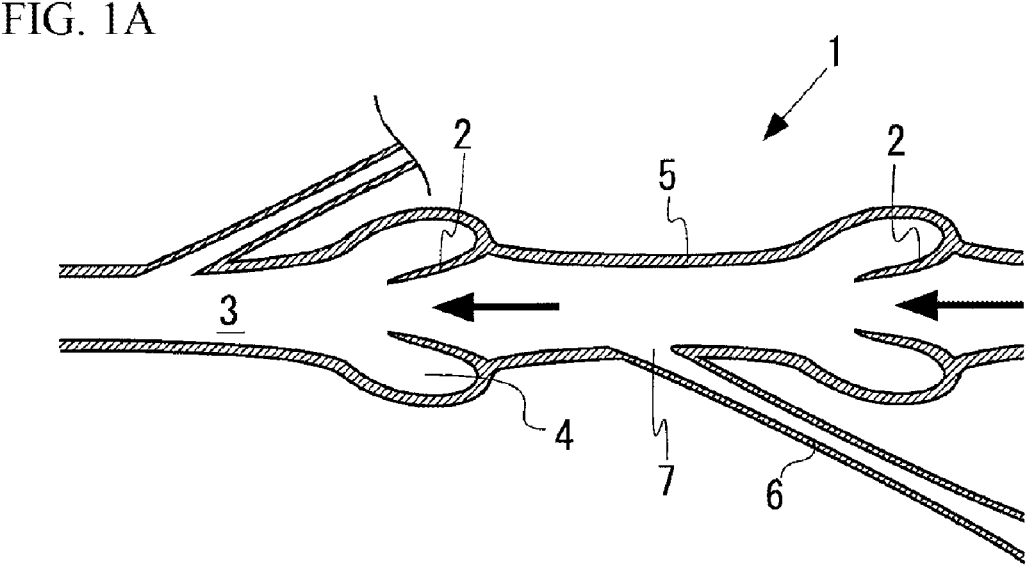
FIGS. 1A and 1B schematically illustrate behavior of a vein 1 and a venous valves 2 for the blood flow. That is.
Figure 1B:
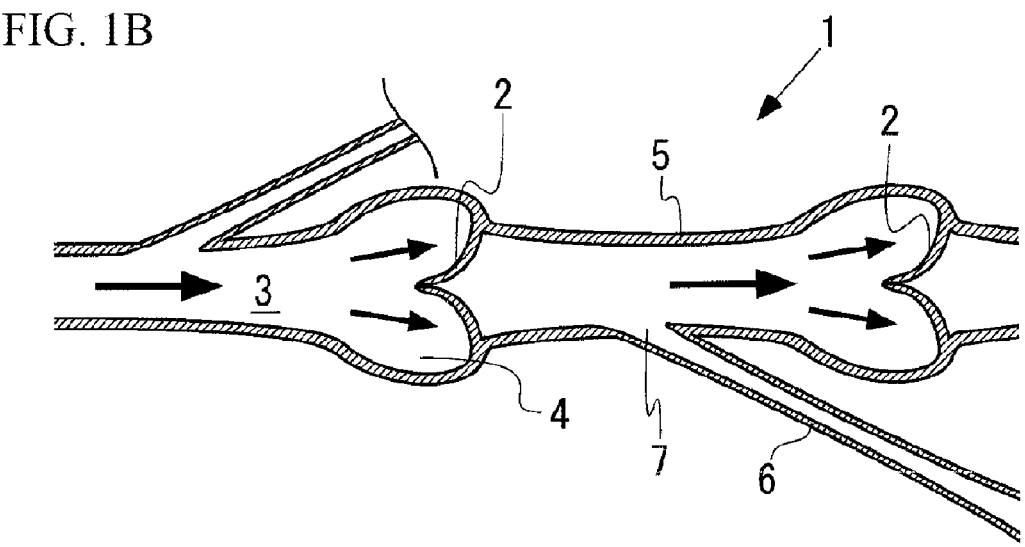
Figure 2A:
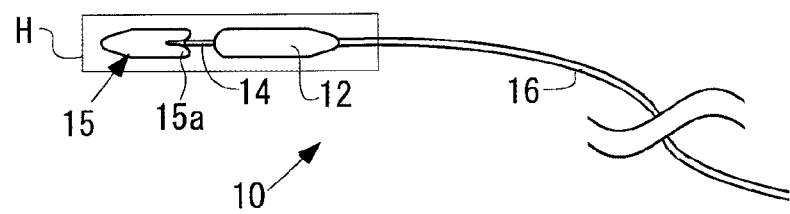
FIGS. 2A to 2E schematically illustrate the conventional venous valve incising cutter 10 disclosed by the patent document 1 and the non-patent document 1. That is.
Figure 2B:
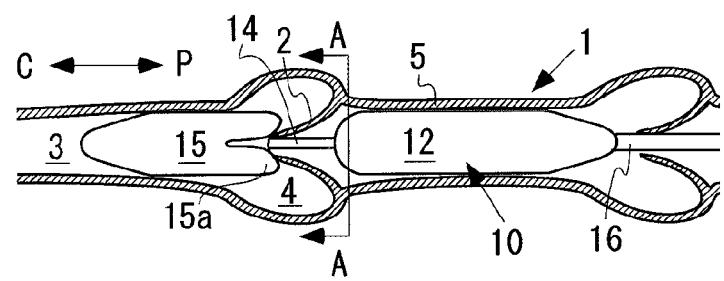
Figure 2C:
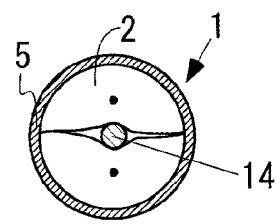
Figure 2D:
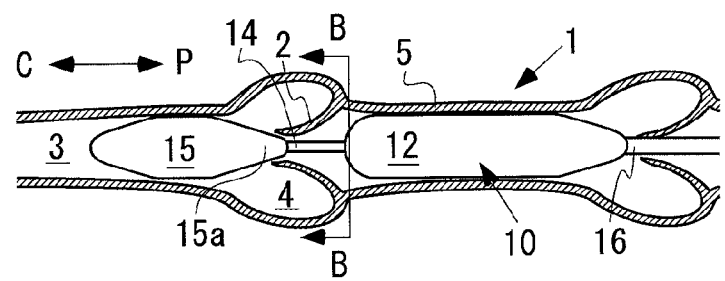
Figure 2E:
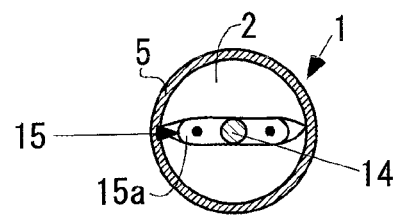

REFERENCE NUMERALS 1 vein or autologous vein; 2 venous valve; 3 lumen; 4 venous valvular sinus; 5 vessel wall; 6 rami; 7 vascular bifurcation; 10 conventional venous cutter; 12 second rod; 14 link rod; 15 first rod; 15a cutting blade; 16 flexible wire; 20, 201, 202, 203, 204 venous valve incising cutter; 22, 22d, 22e, 25d guide; 22a cylindrical surface; 22b, 48 fore portion; 22c, 32 posterior portion; 24 coupling rod; 24a variable length coupling rod; 24b insertion hole; 24c housing hole; 25a main guide; 25b sub-guides; 25c intra-guide coupling rod; 26 wire; 27 coupling spring; 30 cutting teeth head; 34 cutting stabbers; 36 outer surrounding surface; 36a outmost surrounding surface; 38 pyramid surface; 40a outer blade; 40b inner blade; 42 apex; 44 blade end point; 45 incising line; 46 V-cut notch; 51 fore guide portion; 52 posterior guide portion; 53 cylindrical room; 54 taper thread; 55 internal taper thread; C center; P periphery; T axis.

DETAILED DESCRIPTION OF THE INVENTION

Description of the Specific Embodiments

The embodiments regarding the present invention are explained in the following with references of drawings. Same codes, numbers and signs are used for the same and common parts of the venous valve incising cutters and the same and common views thereof in order to avoid redundant explanation.

1. First Embodiment

Figure 3:
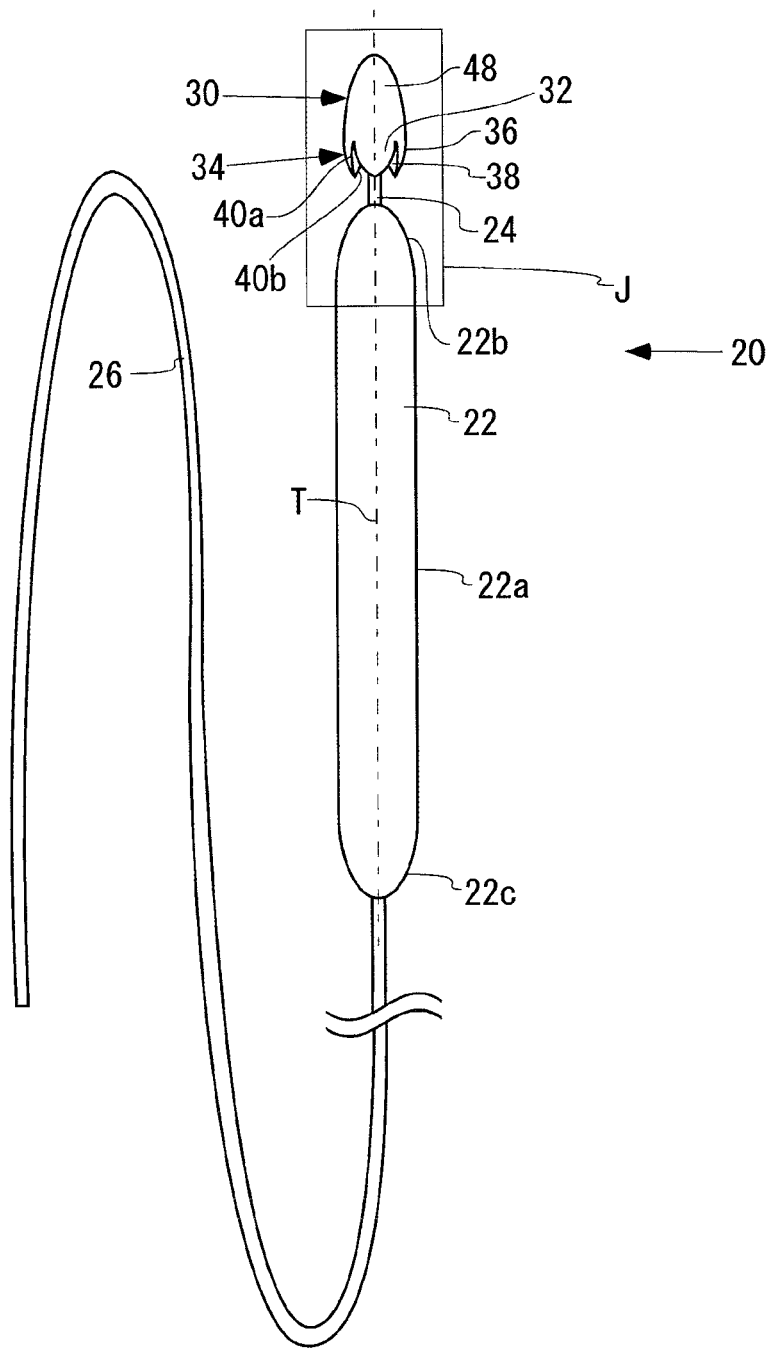
FIG. 3 is a schematic illustrating the whole view of the venous valve incising cutter regarding the present invention.

First of all, FIG. 3 shows the whole view of the venous valve incising cutter 20 regarding the present invention regarding the first embodiment. FIG. 4A shows a zoom-in view of the part surrounded with the rectangular J of the venous valve incising cutter 20 regarding the first embodiment of the present invention.

As shown in FIG. 3, the guide 22 of the venous valve incising cutter 20 is to align itself via the axis T which is common rotational axis and of which direction the vein is aligned. The guide 22 has the shape combined with a cylindrical surface 22a of a cylinder having the axis T of which diameter is smaller than the inner diameter of the vein to which the conventional venous valve incising cutter 10 is inserted, a fore portion 22b and a posterior portion 22c, both of which have a common axis as the axis T. The guide 22 has preferably the shape combined with a cylindrical surface 22a of a cylinder having the axis T of which diameter is smaller than the inner diameter of the vein to which the conventional venous valve incising cutter 10 is inserted, a fore portion 22b and a posterior portion 22c both of which have a hemisphere and/or hemispheroid shape. The shape of the guide 22 is preferably an egg-shape or a lemon-shape.

The venous valve incising cutter 20 can maintain a luminal shape, that prevents an occlusion of the vein 1 to which the venous valve incising cutter 20 is inserted since the venous valve incising cutter 20 has the guide 22. If the venous valve incising cutter 20 has no such guide 22, the vein 1 easily occludes and it is difficult to incise the venous valves 2. On the other hand, such difficulty is solved since the venous valves easily thrust into the gap or the separation length between the cutting teeth head 30 and the guide 22.

The coupling rod 24, of which diameter is smaller than those of the guide 22 and the cutting teeth head 20, is fixed to the fore end of the guide 22 and extends to couple with the cutting teeth head 30. A preferable range of the diameter of the coupling rod 24 is 1/8 to 1/4 of that of the cutting teeth head 30 and 1/9 to 1/3 of that of the guide 22.

When the venous valves 2 are kept opened, the venous valve incising cutter 20 cannot incise the venous valves 2 in principle since the cutting blades (called "cutting stabbers 34" hereinafter) of the cutting teeth head 30 merely pass through the venous valves 22. However, the venous valve incising cutters 20 can incise the venous valves since the diameter of the coupling rod 24 is smaller than either that of the guide 22 or that of the cutting teeth head 30 so that the venous valves 2 close at the gap between the back end of the cutting teeth head 30 and the front end of the guide 22. Therefore the cutting stabbers 34 of the cutting teeth head 30 of the venous valve incising cutter 20 of the present invention can bite and incise the vein valves 2.

The diameter of the cylinder shape body of the guide 22 and the diameter of the shortest axis of the hemispheroid portion of the guide 22 are preferably same as the maximum diameter of the cutting teeth head 30. However, if the guide 22 has a function enabling to dilate a lumen 3 of the vein 2 and make the venous valves 2 close, the other dimensions such that the diameter of the cylinder shape body of the guide 22 or the diameter of the shortest axis of the hemispheroid portion of the guide 22 may be larger or smaller than the maximum diameter of the cutting teeth head 30.

A wire 26 adopted in the present invention has flexible one that is attached to the back end of the guide 22 and extends backwardly. It is preferred that the wire 26 is straight and has no kinks or gurge. It is preferable that the surface of the wire 26 has roughly round shape in the cross section so that it does not damage wall surfaces of veins.

The cutting teeth head 30 has a circle line at the cross section of the portion where the cutting stabbers 34 are formed. The center of the circle line is the cross point of the axis T to the cross section. The maximum diameter of the cutting teeth head 30 is larger than that of the coupling rod.

The cutting teeth head 30 has a posterior portion 32 that has partly a rotational plane inwardly curving to the axis T.

The cutting teeth head 30 has preferably an egg-shape of which round tip is in the front part of the cutting teeth head 30.

The shape of the cutting teeth head 30 may be a fore portion 48 that has a hemispheroid shape and a posterior portion 32 that has hemispheroid or hemisphere shape. The axis toward the front direct of the fore portion 48 is the long axis of the hemispheroid and the long axis coincide with the axis T. The long axis of the hemispheroid or the radius of the hemisphere of the posterior portion 32 is smaller than the long axis of the fore portion 48.

The shape of the cutting teeth head 30 may be a combined shape of above hemispheroid of the fore portion 48 directly coupling with above hemispheroid or hemisphere of the posterior portion 32 like as an egg-shape or that of above hemispheroid of the fore portion 48 directly coupling with above hemispheroid or hemisphere of the posterior portion 32 and a circular cylinder coupling therebetween.

The projection view of the cutting teeth head 30 (that is, a view from the arrow K in FIG. 4A) is same from any view point around the axis T. Therefore, wherever the vascular bifurcation locates against or comes close to the cutting teeth head 30, the outer surrounding surface 36 blocks the vascular bifurcation coming close to the apex 42 of the cutting teeth head 30. According to this configuration such as the shape of the cutting teeth head 30 and inclusion of more than four cutting stabbers 34, the venous valve incising cutters 20 of the present invention can prevent to rupture veins.

The maximum diameter of the cutting teeth head 30 is preferably from 2.0 mm to 5.0 mm and 3.0 mm is mostly preferred for the ease of treatment and the sizes of veins to be treated. However, another maximum diameter, that is larger or smaller than the above range as 2.0 mm to 5.0 mm, can be adopted in accordance to the dimension of lumen 3 of the vein 1.

In the posterior portion 32, more than four cutting stabbers 34 that have apexes 42 facing to the guide 22 and roughly triangular pyramid shapes are formed around the cutting teeth head with an equal separation distance each other. Each apex is formed in the outer surrounding surface 36 of the cutting teeth head and two ridges formed on the outer surrounding surface 36 from the apex construct blades (called "outer blades", hereinafter) 40a and one ridge formed from the apex in the inner part of the cutting teeth head 30 does a blade (called a "inner blade", hereinafter) 40b. According to this physical design of the cutting stabbers 34, the cutting edges of the cutting teeth head 30, especially outer blades 40a, locate around the surface thereof.

The venous valve incising cutter 20 of the present invention can cut the venous valves 2 like as surgical knives or scissors by the outer blades 40a and the inner blades 40b which three ridges of the cutting stabbers 34 form and function.

It is preferable that the posterior portion 32 has four to eight cutting stabbers 34. And four cutting stabbers are mostly preferred since the fewer the stabbers are the easier the selvage thrust into the posterior portion 32 of the cutting teeth head 30 and the more than four of the cutting stabbers 34 the more surely the cutting teeth head 30 destroy the venous valves. Whatever rotational angle the venous valve incising cutter 20 is inserted into the vein with, it is possible to surely incise the venous valves. The even pieces of the stabbers 34 are preferred to be formed in the cutting teeth head 30 since the manufacturing process to form even pieces of stabbers 34 is simpler than that to form odd pieces thereof.

The inner blade 40b is formed by the ridge 40 of the two pyramid surfaces 38, each of which includes an apex 42, two blade end points 44 on the outer surrounding surface 36 and the other blade end point in the axis T, that is common to other pyramid surfaces 38.

The inner blade 40b straightly directs to the common point in the axis T.

The outer blades 40a are formed by the ridges 40 formed on the outer surrounding surface 36 surrounding of the cutting teeth head 30. Since the distance between the adjacent apexes 42 is shorter than that of the separation distance between two base centers of the adjacent stabbers 34 due to the taper shape of the posterior portion 32 of the cutting teeth head 30 toward the apexes 42 of the stabbers 42, a vascular bifurcation 7 of the branching vessel 6 hardly thrust into an interspace between two outer blades 40a of the adjacent stabbers 34.

Since the apexes 42 of the stabbers 34 comprising two pyramid surfaces 38 are inner side from the outmost surrounding surface 36a of the cutting teeth head 30, this physical design prevents the apexes 42 to catch the vascular bifurcation 7 of the branching vessel 6 (see FIG. 5D).

The apexes 42 of the stabbers 34 regarding the first embodiment are sharp knife points. Therefore, the surgeons can easily stick the venous valves 2 which are thin and soft with the venous valve incising cutter 20 regarding the present invention.

The outer blades 40a are continuously formed around the outer surrounding surface 36 of the cutting teeth head 30.

The blade end points 44 of adjacent two outer blades 40a, which locate in about middle part of the cutting teeth head 30, are preferably formed in the outmost surrounding surface 36a of the cutting teeth head 30. However, the blade end points 44 of adjacent two outer blades 40a, may be formed in the front or back side against the outmost surrounding surface 36a of the cutting teeth head 30. The blade end points 44 commonly terminates one from a ridge and the other from an adjacent ridge thereof.

As for the cutting teeth head 30, the maximum diameter, the position of the apexes 42 relevant to other parts, the curved surface of the posterior portion 32 and the separation distance from the guide 22 are discussed in the following paragraphs.

Assuming the maximum diameter of the cutting teeth head 30 be x, the distance between the axis T and the apexes 42 of the cutting stabbers 34 $y$, the distance between the apexes 42 and the top end of the guide 22 $h$, the distance between the apexes 42 and the position or the maximum diameter of the cutting teeth head 30 projected on the axis T $z$, the relation of these physical parameters are preferred that y/x is 1/3 to 1/2, z/2x 0.8 to 1.3 and x/h more than 1.3.

In addition, it is most preferred that y/x is 2/3 and z/2x 1.0 to 1.125. As for x/h, 1.5 is the most preferable number, however x/h may be more than or less than 1.5 in response to the diameter, elasticity and expandability of the vein 1 (an autologous vein). It is preferred that x/h is equal to or larger than 1.5 or z/h is from 0.81 to 0.89 in order to prevent the vascular bifurcation 7 of the branching vessel thrusting into gaps between adjacent cutting stabbers 34 through the constriction between the posterior portion 32 of the cutting teeth head 30 and fore portion of the guide 22.

The manufacturing method of the venous valve incising cutter 20 regarding the first embodiment is discussed in the following paragraphs. In the process 1, the cutting teeth head 30 is formed by molding or rotation milling into the shape of a hemispheroid, an egg or a combination of a hemispheroid and hemisphere. Other processes such as 3D printer or casting etc. are adopted for the process 1 depending on the quantity, cost and availability.

In the process 2, the posterior portion 32 of the cutting teeth head 30 formed in the process 1 is V-cut several times from different rotational angle to the axis T. For the shape of cutting teeth head 30 shown in FIGS. 4A and 4B, two V-cut notches 46 in 90 degrees angle difference in the rotational angle to the axis T can form four cutting stabbers 34. The process that is more times than twice V-cutting may be accepted for the cutting teeth head 30 that has more cutting stabbers 34 than four cutting stabbers 34. The other cutting shape than V-cut notch 46, may be adopted for the V-cutting at the posterior portion 32 of the cutting teeth head 30.

In the process 3, the bottom end of the posterior portion 32 of the cutting teeth head 30 is connected with the front end of the coupling rod 24 of which back end is connected with the front end of the guide 22. A wire 26 which is flexible is connected to the bottom end of the guide 22. Thermal insertion is preferred for coupling two parts if they are made of metal. Other connection methodologies are adopted as long as bio-compatible materials are used.

Another connection of the wire 26, such that the guide has a longitudinal through-hole to which the wire 26 is inserted and fixed therein and the top end of the wire 26 is connected to the bottom end of the posterior portion 32 of the cutting teeth head 30 that alternates the coupling rod 24, may be adopted for connecting the cutting teeth head 30, the guide 24 and the wire 26.

A treatment method using the venous valve incising cutter 20 regarding the first embodiment is explained with an example of non-reverse treatment in the following paragraphs. The venous valve incising cutter 20 regarding the first embodiment can be of cause used for in-situ treatment.

Though the following explanation is about artery revascularization treatment, the venous valve incising cutter 20 regarding the first embodiment may be used for other surgical treatments such as surgically-placed shunt or coronary surgery using an autologous vein as a graft.

FIGS. 5A to 5D show explanatory schematics to use coronary surgery in time series from FIG. 5A to FIG. 5D. The following method to use the venous valve incising cutter 20 is called first treatment method. The progressive steps corresponding to FIGS. 5A to 5D are called as Step 1 to Step 5, hereinafter.

In Step 1, the surgeon cut a necessary portion of vein 1 out from lining membrane to be excised and the central portion of the vein 1 as cut as a graft of an autologous vein is anastomosed to the central portion of the artery, that is, just at an upper part from the occluded part of the artery.

In Step 2, the surgeon confirms the position of the venous valves 2 in the harvested vein. After anastomosis, the arterial blood flows into the vein 1 (an autologous vein) up to the venous valve 2 which exists in the most central side of the center C and does not flow therethrough. Therefore, the surgeon can perceive the pulses by touching the center C side of the venous valve 2 that locates in the most central side and cannot by touching the periphery P side thereof. By such perception of the palpable pulses, the surgeon can confirm the position of the venous valve 2 of the harvested vein.

In Step 3, the surgeon inserts the venous valve incising cutter 20 regarding the first embodiment inside the lumen 3 of the vein 1 as shown in FIG. 5A and inserts the venous valve incising cutter 20 forward until the fore portion of the guide 22 reaches the center C side of the venous valve 2 that locates in the most central side as shown in FIG. 5B. Since the venous valve 2 closes against the blood flow from the center C to the periphery P, the venous valve incising cutter 20 is not blocked by the venous valve 2 such that the fore portion 48 of the cutting teeth head 30 and the fore portion of the guide 22 thrust into and pass through the venous vein 2 and can move through the vein 1.

In Step 4, after confirming the fore portion of the guide 22 has reached the center C side of the venous valve 2 that locates in the most central side, the surgeon pulls the wire 26 outwardly. Then the venous valve 2 closes at the constriction between the posterior portion 32 of the cutting teeth head 30 and the fore portion of the guide 22, that is, the portion of the coupling rod 24. The diameter of the constriction is smaller than those of the posterior portion 32 of the cutting teeth head 30 and the fore portion of the guide 22. The surgeon can perceive closing of the venous valve 2 by tactile perception of his fingertips so that he can confirm that the cutting teeth head 30 is caught at the venous valve 2.

In Step 5, the surgeon further pull the wire 26 and then the apexes 42 of the cutting stabbers 34 of the cutting teeth head 30 stick the venous valve 2. The venous valve 2 is incised along the three ridges of the cutting stabber 34 that sticks thereof. The surgeon can perceive the insection of the venous valve 2 by tactile perception of his fingertips and can confirm the completion of the insection by the perception of the palpable pulses conducted through the artery blood through tactile perception of finger tips.

In Step 6, the surgeon pulls the wire 26 so that the venous valve incising cutter 20 moves to the next venous valve 2 that locates in the periphery P side from the previous one of which position is determined in a way that the surgeon can perceive the pulses by touching the venous valve 2 that locates in the next periphery P side and cannot perceive the pulses by touching the periphery P side thereof. The surgeon pulls the wire 26 outwardly after confirming the position of the venous valve 2 like as in the same way as Step 2 and repeat Step 3 to Step 5 until the artery blood comes out from the cut end of the vein 1 (an autologous vein). The surgeon can confirm all vein valves 2 have been incised.

In Step 7, the surgeon anastomoses the cut end in the periphery side of the harvested vein 1 (an autologous vein) to the artery, that is, just a lower part from the occluded part of the artery.

A sequence of these steps using the venous valve incising cutter 20 enables to incise the venous valve 2 in one operation such that the guide 22 is pushed to open the closed venous valve 2 in passing therethrough by pulling the wire 26, the venous valve 2 closes from opening by further pulling the wire 26 and the cutting stabbers 34 of the venous valve incising cutter 20 finally incise the closed venous valve 2.

In the surgical steps, the venous valve incising cutter 20 is inserted in the vein 1 up to the guide 22 reaches the center C side of the venous valve 2 that locates in the most central side and then continuously pulled out to incise all venous valves 2 in series so that the one action of insertion and withdrawal of the venous valve incising cutter 20 enables the surgeon to complete incising of all venous valves included in the vein 1 as cut as an autologous vein. After such incising, the surgeon anastomoses the cut end of the periphery side of the vein 1 (an autologous vein) to the artery, that is, just a lower part from the occluded part of the artery by which the surgeon makes a bypass flow of artery blood bypassing the occluded part of the artery and the revascularization is completed.

The function of the venous valve incising cutter 20 regarding the present invention is discussed in the following paragraphs.

Figure 6A:
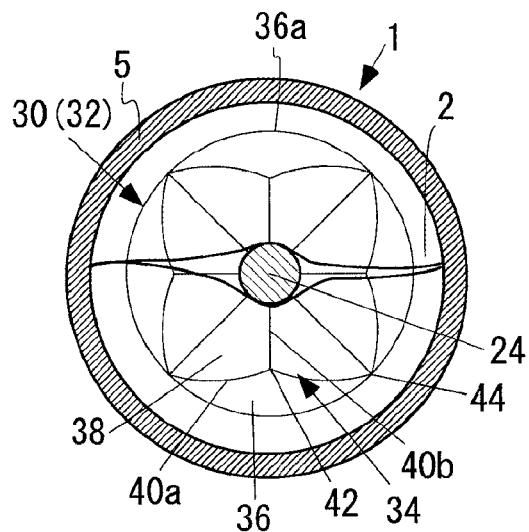
FIGS. 6A to 6D schematically illustrate the function of the venous valve incising cutter regarding the first embodiment. That is.
Figure 6B:
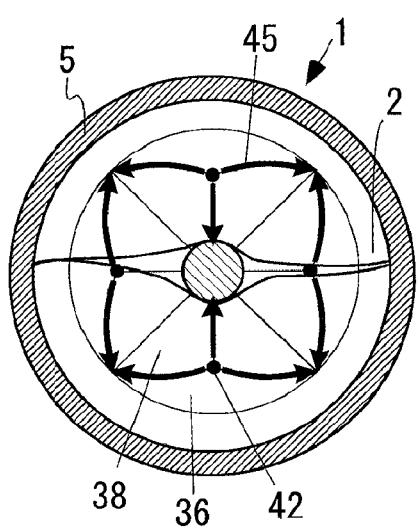
Figure 6C:
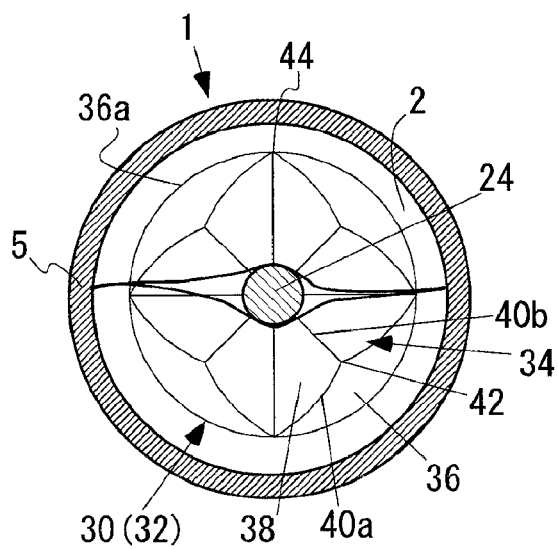
Figure 6D:
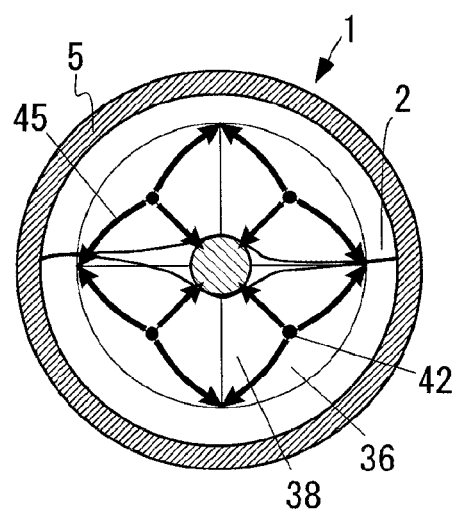

FIGS. 6A to 6D show the function of the venous valve incising cutter 20 regarding the first embodiment. FIG. 6A is a schematic taken in a view of the direction to arrows "D" in FIG. 5C. FIG. 6B is a schematic explaining the function of the venous valve incising cutter 20 regarding the present invention. FIG. 6C is a schematic taken in a view of the direction to arrows "D" in FIG. 5C in the case that the venous valve incising cutter 20 regarding the present invention is rotated in 45 degrees angle. FIG. 6D is a schematic explaining the function of the venous valve incising cutter 20 in the state shown in FIG. 6C.

For the purpose of clear explanation, the guide 22 is not shown and the outline of the cutting teeth head 30 is drawn in fine lines. The black circles drawn in FIGS. 6B and 6D show the positions of the apexes 42 of the cutting stabbers 34.

For the venous valve incising cutter 20, the outer blades 40*a* are formed all therearound. The blade end points 44 of adjacent two outer blades 40*a* are on the surface of the cutting teeth head 30 and in the maximum diameter cross sectional plane the cutting teeth head 30. The blade end points 44 are also common to the adjacent out blades 40*a*. Therefore, once the apexes 42 stick to the venous valves 2, then the venous valve incising cutter 20 cut the venous valves 2 along from the apexes 42 to the blade end points 44. Each outer blade 40*a* incises the venous valve 2 in a segment of a incising line 45 so that all segments of the incising lines 45 make a continuous incising line over the venous valves 2. Since the continuous incising line covers the most range of the venous valve 2, one pass of the venous valve incising cutter 20 through the venous valve 2 can destroy the function thereof, that is, to block the blood flow from the center C side to the periphery P side.

By using the venous valve incising cutter 20 on the present invention, it is possible that a simple treatment that the cutting teeth head 30 passing by the venous valve 2 in one round passing can complete a treatment of artery revascularization, which provides less incidental damages to the vessel tissues such as vessel endothelium and branching vessels 6.

As shown in FIGS. 6B and 6D, the venous valve incising cutter 20 has four inner blades 40*b* from the four apexes 42 to the axis T. Therefore, at least two of the inner blades 40*b* can incise the selvages of the venous valve 2 whatever angle the venous valve incising cutter 20 is inserted in the vein 1 with. Once the selvages of the vein 1 are cut, the venous valve 2 easily opens toward the periphery P and loses the function to block the blood flow from the center C to the periphery P.

2. Second Embodiment

Figure 7:
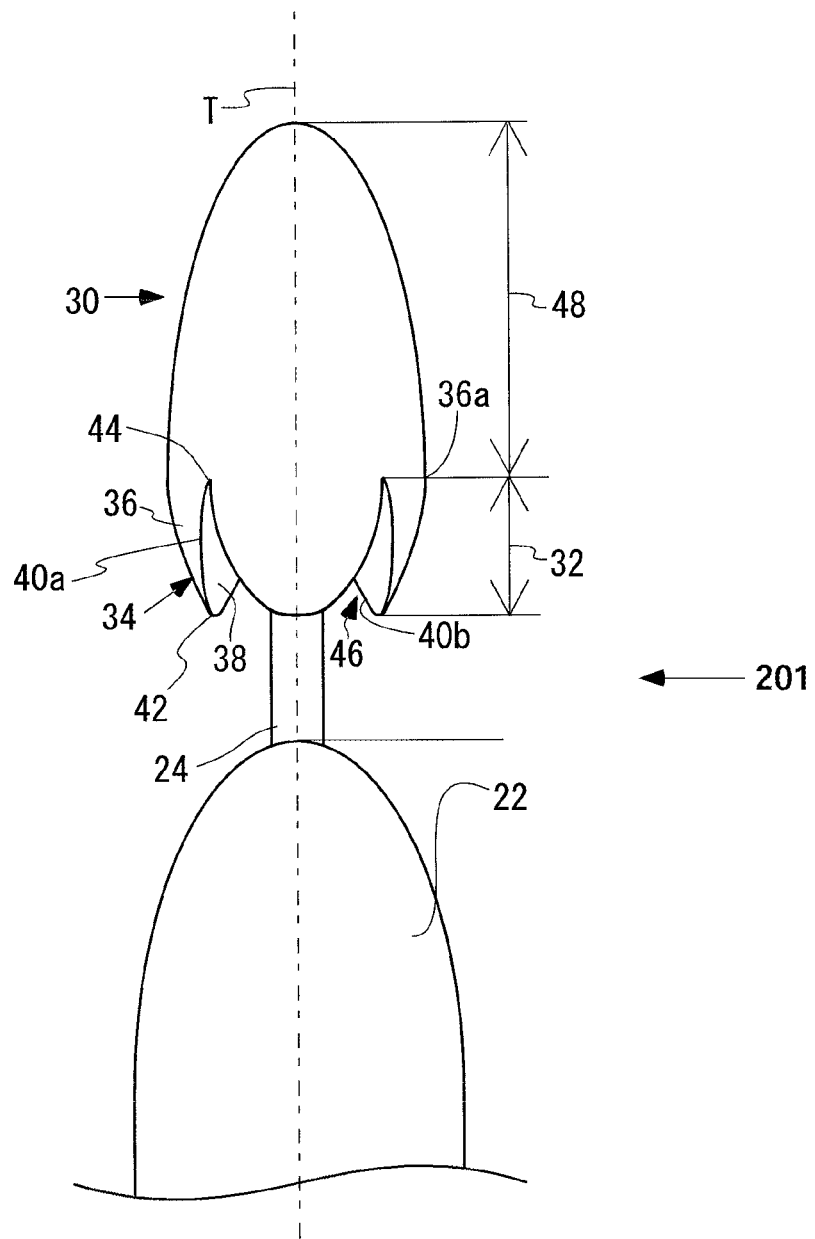
FIG. 7 is a schematic of a zoom-in view of the venous valve incising cutter regarding the second embodiment corresponding to the part surrounded with the rectangular J in FIG. 3.

The venous valve incising cutter 201 regarding the second embodiment of the present invention is discussed in the following. FIG. 7 is a schematic of the zoom-in view of the venous valve incising cutter 201 corresponding to the J part shown in FIG. 3.

The vessel walls of veins have venous valves that prevent turbulence of blood flow as seen in arteries so that the veins have few irregular form on the vessel walls. Therefore, the cutting stabbers 34 of the first embodiment scarcely stick irregular vessel walls even the cutting stabbers 34 have knife-points formed by the apexes 42. However, since the vessel walls of veins are rather thin, the inner shape of vein lumen tends to vary, by the external pressure or the existence of muscle or other organs, to non-circular ones or deformed ones that impede a smooth blood flows. In such particular cases, there is a risk that the apexes 42 of the cutting stabbers 34 may damage the vessel walls of the vein 1.

To prevent such an incidental damages onto the vessel walls, the venous valve incising cutter 201 regarding the second embodiment of the present invention adopts a round apexes 42 of the cutting stabbers 34. The rest portions of the outer blades 40*a* other than the round apexes 42 are on the outer surrounding surface 36 of the cutting teeth head 30.

The other construction, the method of use and the functions of the venous valve incising cutter 201 are same as those of the venous valve incising cutter 20 in the first embodiment.

The manufacturing method of the venous valve incising cutter 201 of the second embodiment is discussed in the following. FIG. 7 is a schematic of a zoom-in view of the venous valve incising cutter 201 corresponding to the J part shown in FIG. 3.

The apexes 42 of the venous valve incising cutter 201 of the second embodiment of the present invention is provided by the venous valve incising cutter 20 in the first embodiment of which apexes 42 are cut by files or other cutting tools. For example the ridge line of adjacent pyramid surfaces 38 is filed downwardly in external direction. As the result, the plane formed by filing and the surface of hemispheroid or hemisphere shape of the posterior portion 32 of the cutting teeth head 30 form a round ridge or a non-knife-point blade as the line of intersection of these surfaces. The round ridges or the non-knife point blades meade by the above process have small planar areas positioning around the apexes 42 of the cutting stabbers 34. The apexes 42 are no more knife-point or sharp cut incising blades, however the planar areas are small and the overall shape of the cutting stabbers 34 can still be a roughly triangular pyramid. In other words, the above manufacturing method includes the manufacturing method of the venous valve incising cutter 20 regarding the first embodiment and a further process in order to cut the knife-point 42 and a vicinity thereof in a plane with an different inclined angle to the axis T from the angle that a ridge line 40b, being formed by crossing of the two planes 38 formed in the reverse side of the outer surrounding surface 36 of the cutting teeth head 30, has to the axis T.

The treatment method and manufacturing method of the venous valve incising cutter 201 of the second embodiment are same as those of the venous valve incising cutter 20 of the first second embodiment.

3. Third Embodiment

Figure 8:
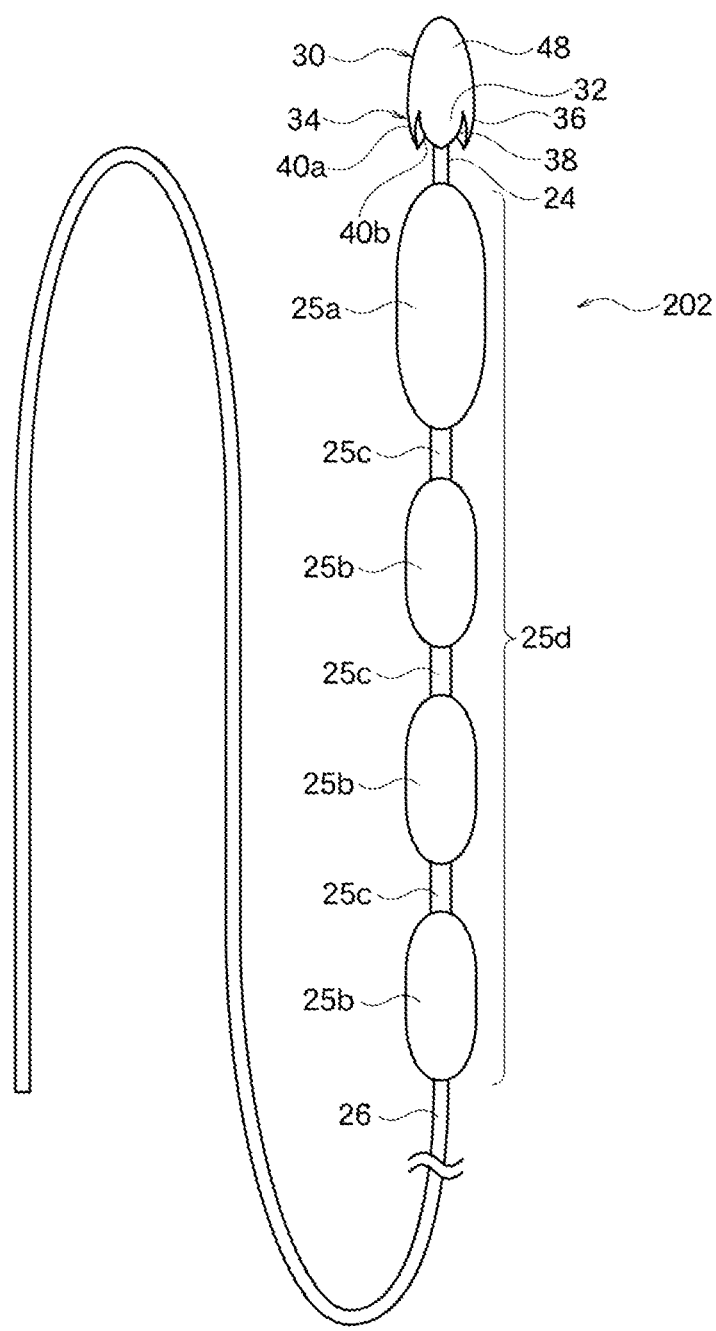
FIG. 8 is a schematic illustrating the whole view of the venous valve incising cutter regarding the third invention.

The venous valve incising cutter 202 regarding the third embodiment of the present invention is discussed in the following. FIG. 8 is a schematic of overall view of the venous valve incising cutter 202.

The venous valve incising cutter 202 regarding the third embodiment has a main guide 25a, one or more sub-guides 25b and intra-guide coupling rods 25c as substitute for the guide 22 that has a single body in the venous valve incising cutter 20 regarding the first embodiment. The main guide 25a has a hemispheroid or hemisphere shapes in the fore and posterior portions and a cylinder shape therebetween and the sub-guide 25b has the similar shape to that of the main guide 25a.

The venous valve incising cutter 20 regarding the first embodiment of the present invention has rather long guide 20 and the vessel walls of veins 1 are rather thin in comparison to arteries. Therefore, when the surgeon inserts the venous valve incising cutter 20 into the vein 1, the vein 1 can be often physically damaged in the insertion process since the elongation of the vein 1 does not conform to the straightness of the guide 20, in other words, the vein 1 is usually not as straight as the guide 20 is. The outer surrounding surface 36 of the middle portion of the guide 20 is simply a cylindrical surface straight along about the length thereof. Therefore, the friction between the surface of the guide 20 and inner wall of the view 1 and the pincer grasp of the vein 1 to which the guide 20 is inserted tends to give physical damages to the vein 1.

Since the guide 25d of the venous valve incising cutter 202 regarding the third embodiment of the present invention includes the main guide 25a, one or more sub-guides 25b and intra-guide coupling rods 25c that couple the main guide 25a and one or more sub-guides 25b, the guide 25d has as a whole flexibility due to elasticity of, especially, the intra-guide coupling rods 25c. Therefore the venous valve incising cutter 202 can easily fit to the longitudinal curvature of the vein 1 and smoothly move therein in comparison to the venous valve incising cutter 20 of the first embodiment and the external force to the insertion make less damage to the vein 1.

Since the intra-guide coupling rods 25c do not contact with the wall of the vein 1, the venous valve incising cutter 202 has little friction with the vein 1 and smoothly get into inside of the vein 1 when it is inserted thereinto.

The intra-guide coupling rods 25c are used for the guide 25d, the volume of the guide 25d is smaller than those of the guide 22 which is made of a bulk material. Therefore the guide 25d is lighter than the guide 22. It is easier for surgeons to perceive the frictional force through tactile perception of fingertips when he/she inserts the venous valve incising cutters 202 into the vein 1 and the surgeons can avoid the risk to apply over force for inserting the venous valve incising cutters 202 into the vein 1.

As discussed above, the venous valve incising cutters 202 enables to be easily inserted into the vein 1 and gives less damage thereto due to such characteristics as flexibility, little friction and light weight. Therefore, the vein 1 (an autologous vein) to revascularize the artery by vein grafting receives little damages when artery blood flows therethrough and stable and reliable blood circulation is provided to the patients suffering circulatory diseases. The main guide 25a and the sub-guides 25b have solid revolution shapes and the diameter of the main guide 25a may be larger or smaller than the maximum diameter of the cutting teeth head 30 like as the venous valve incising cutters 20 of the first embodiment. On the other hand, the configuration of the guide 25d is for the purpose of reducing friction with the vessel wall of the vein 1. Therefore it is preferable that the diameters of the sub-guides 25b are equal to or smaller than that of the main guide 25a. The treatment method to use the venous valve incising cutters 202 is same as that of the venous valve incising cutters 20 of the first embodiment.

The manufacturing method of the venous valve incising cutters 202 of the third embodiment is explained in the following paragraph.

The process 1 and the process 2 of the manufacturing method for the venous valve incising cutters 202 are same as the process 1 and process 2 of that for the venous valve incising cutters 20, respectively. However, in the process 3 of the manufacturing method for the venous valve incising cutters 202, the back end of the cutting teeth head 30 and the front end of the coupling rod 24 and the back end of the coupling rod 24 and the front end of the main guide 25a are connected as well. Moreover, the back end of the main guide 25a and the front end of the sub-guide 25b are connected with the intra-guide coupling guide 25c. When more than two sub-guides 25b are used for the venous valve incising cutters 202, the back end of the sub-guide 25b and the front end of the next sub-guide 25b are connected with another intra-guide coupling guide 25c until all sub-guides 25b are connected with other intra-guide coupling guides 25c in a sequence. The back end of the last sub-guide 25b and the front end of the wire 26 are connected. If the cutting teeth head 30, the coupling rod 24, the main guide 25a, the intra-guide coupling rods 25c, the sub-guides 25b and the wire 26 are all made of metals, thermal insertion is preferred for coupling these parts. Other connection methodologies are adopted as long as bio-compatible materials are used.

4. Forth Embodiment

Figure 10:
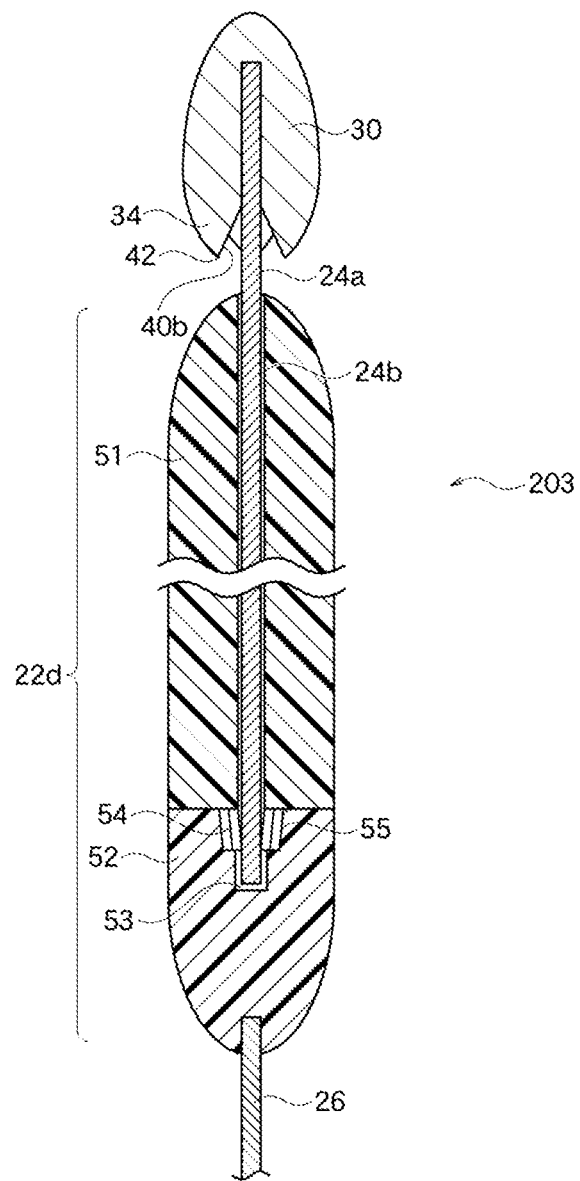
FIG. 10 is a schematic illustrating the whole view of the venous valve incising cutter regarding the fourth embodiment.

The venous valve incising cutter 203 regarding the fourth embodiment of the present invention is discussed in the following. FIG. 10 is a schematic illustrating the whole view of the venous valve incising cutter regarding the fourth embodiment.

In the venous valve incising cutter 20 regarding the first embodiment, for the purpose that the cutting teeth head 30 of the venous valve incising cutter 20 does not damage the vessel endothelium, the vascular bifurcation of the branching vessel or irregular vessel walls, the distance h between the apexes 42 cutting stabbers 34 and the front end of the guide 22 is limited relative to the maximum radius of the cutting teeth head 30 so that the salvage or fringes thereof hardly thrust into the gap between the cutting stabbers 34 and the front end of the guide 22.

Figure 9:
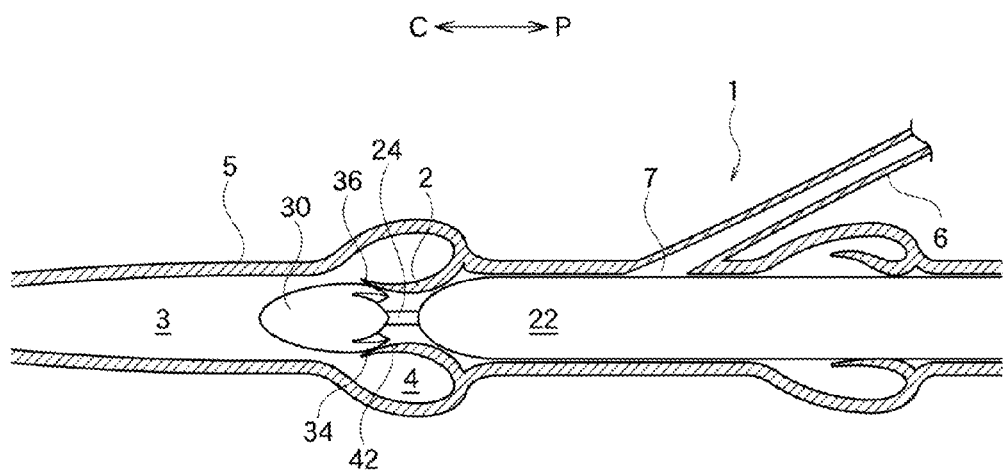
FIG. 9 is a schematic illustrating an example of interference of the venous valve incising cutter against the venous valves in the vein.

Due to such dimensional limitation, the venous valve 2 sometime, as shown in FIG. 9, does not thrust into the gap between the back end of the cutting teeth head and the front end of the guide 22 depending on the shape of the venous valve 2 and the distance h, even when the venous valve incising cutter 20 gets close to the venous valve 2 to be incised and the venous valve 2 positions therebetween. When the venous valve incising cutter 20 horns on the venous valve 2 in such an interference, it is not possible to incise the venous valve 2 by drawing the venous valve incising cutter 20 out from the vein 1.

Besides the above assemblage, the venous valve incising cutter 203 regarding the fourth embodiment has the same configuration as the venous valve incising cutter 20 regarding the first embodiment. The use of taper threads 54 and 55 and the divided body of the guide 22d is to realize the adjustability to adjust the gap or the separation length between the cutting teeth head 30 and a guide 22d. Another composing or configuration is acceptable provided the adjustability is ensured.

For the adjustment of the gap or the separation length (that is, h) between the cutting teeth head 30 and a guide 22d, the variable length coupling rod 24a enables to move against the guide 22d by loosening the internal taper thread 55 and the separation length therebetween. For the adjustment, h is properly determined and set in such a length that the venous valves 2 easily thrust into the gap between the cutting teeth head 30 and the guide 22d but the cutting teeth head 30 does not damage vessel endothelium, irregular vessel wall or vascular bifurcation of the branching vessel in the vein into which the venous valve incising cutter 203 is inserted.

As explained above, the venous valve incising cutter 203 in the fourth embodiment can incise the venous valves 2 by adjusting the gap or the separation length between the cutting teeth head 30 and a guide 22d to meet the figuration of the vein 1 such as vessel endothelium, irregular vessel wall or vascular bifurcation of the branching vessel so that the cutting teeth head 30 of vessel endothelium, irregular vessel wall or vascular bifurcation of the branching vessel does not damage the vein 1.

The treatment method using the venous valve incising cutter 203 in the fourth embodiment is same as that of the venous valve incising cutter 20 in the first embodiment except for having a preparatory step to adjust the gap or the separation length between the cutting teeth head 30 and the guide 22d.

The manufacturing method of the venous valve incising cutters 203 of the fourth embodiment is explained in the follow paragraphs.

The process 1 and the process 2 of the manufacturing method for the venous valve incising cutters 203 are same as the process 1 and process 2 of that for the venous valve incising cutters 20, respectively.

In the process 3 of the manufacturing method for the venous valve incising cutters 203, a variable length coupling rod 24a which is longer that the coupling rod 24 used for the venous valve incising cutters 20 is used as substitute therefore. The guide 22d is formed by molding or rotation milling into a dived shape as the fore guide portion 51 and the posterior guide portion 52. An insertion hole 24b in the rotational axis through which a variable length coupling rod 24a is inserted is drilled throughout the fore guide portion 51. A taper thread 54 is formed in the back end of the fore guide portion 51 facing to the posterior guide portion 52. A cylindrical room 53 to keep the rest of the variable length coupling rod 24a and an internal taper thread 55 that is to be screwed together with the taper thread 54 are formed in the posterior guide portion 52 facing to the fore guide portion 51.

The variable length coupling rod 24a is inserted into the insertion hole 24b and is fixed to the guide 22d by screwing the internal taper thread 55 together with rotating the posterior guide portion 52.

In the process 4, the front end of the wire 26 is connected to the back end of the posterior guide portion 52. If the cutting teeth head 30, the variable length coupling rod 24a, the posterior guide portion 52 and the wire 26 are all made of metals, thermal insertion is preferred for coupling these parts. Other connection methodologies are adopted as long as bio-compatible materials are used.

5. Fifth Embodiment

The venous valve incising cutter 204 regarding the fifth embodiment of the present invention is discussed in the following.

In the fourth embodiment, the coupling rod 24 enables to move through the guide 22d and the gap or the separation length between the cutting teeth head 30 and a guide 22d can be appropriately adjusted so that the venous valves 2 easily thrust into the gap between the cutting teeth head 30 and the guide 22d but the cutting teeth head 30 does not damage vessel endothelium, irregular vessel wall or vascular bifurcation of the branching vessel in the vein into which the venous valve incising cutter 203 is inserted.

However, in order to adjust the gap or the separation length between the cutting teeth head 30 and a guide 22d, it is required to loosen the taper thread 54 and the internal taper thread 55 for the variable length coupling rod 24a movable to the guide 22d by re-screwing both the fore guide portion 51 and the posterior guide portion 52 to which the taper thread 54 and the internal taper thread 55 are formed, respectively. This implies that the venous valve incising cutter 203 has to be drawn out from the vein for the adjustment in case when the gap between the cutting teeth head 30 and the guide 22d (that is the distance h) needs adjustment after the venous valve incising cutter 203 is inserted in the vein. This repetitive step causes a risk to damage the vein.

Therefore, a mechanism to adjust h is required under the state that the venous valve incising cutter is inserted in the vein once it has been inserted in.

Figures 11A, 11B:
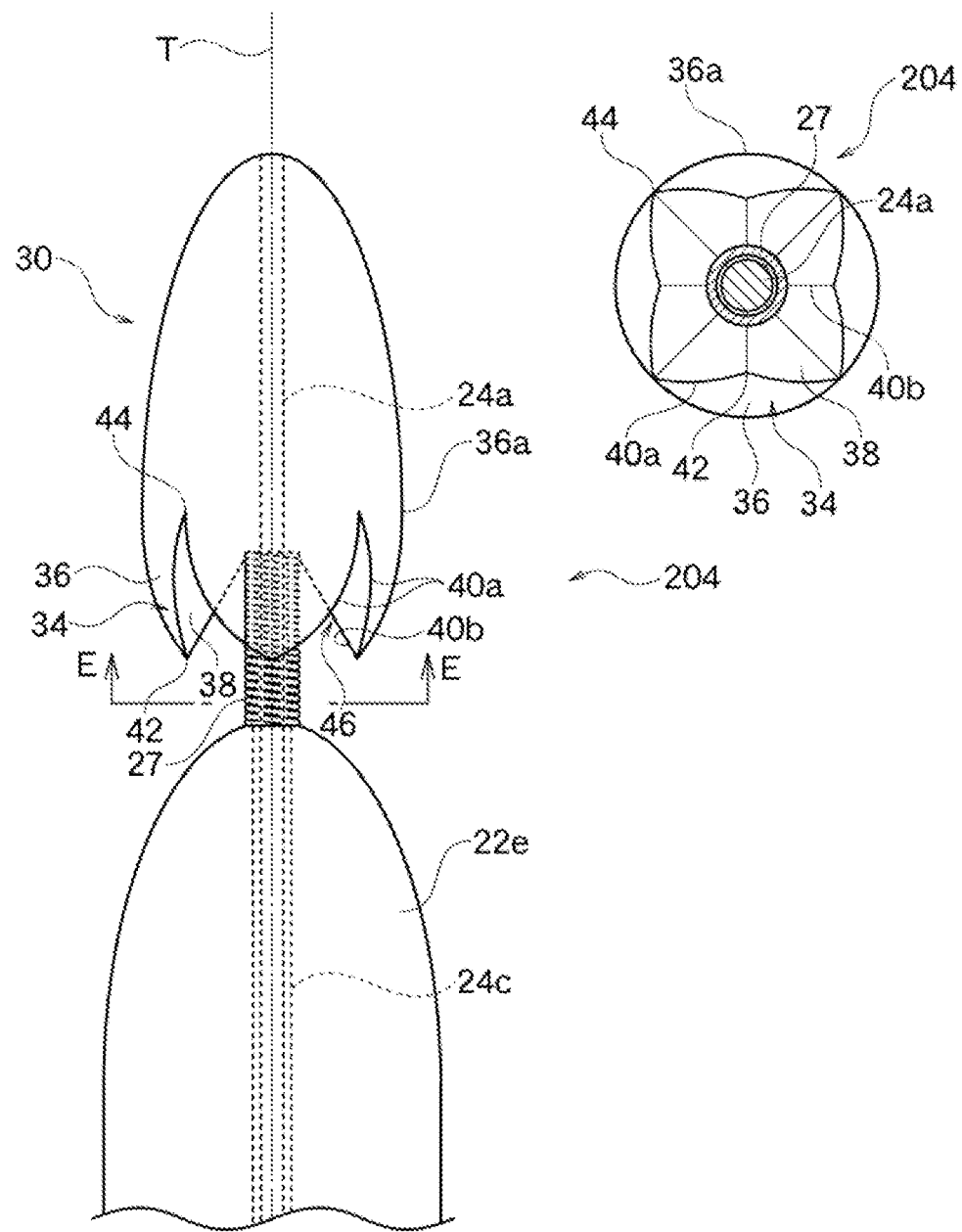
FIGS. 11A and 11B schematically illustrate the whole view of the venous valve incising cutter regarding the fifth embodiment of the present invention. That is.

The venous valve incising cutter 204 regarding the fifth embodiment of the present invention is shown in FIGS. 11A and 11B. FIG. 11B is a schematic showing a fragmentary view taken in the direction of the arrows "E" of FIG. 11A.

The venous valve incising cutter 204 regarding the fifth embodiment, a variable length coupling rod 24a and a coupling spring 27 to couple the cutting teeth head 30 and the guide 22e as shown in FIG. 11A for the coupling means adopted for the venous valve incising cutter 20 regarding the first embodiment, as substitute for the coupling rod 24 that fixes coupling between the cutting teeth head 30 and the guide 22. Due to this mechanism, the cutting teeth head 30 and the guide 22e are couple in an extensible fashion. Other than this mechanism, the venous valve incising cutter 204 regarding the fifth embodiment has the same configuration with the venous valve incising cutter 20 regarding the first embodiment, The variable length coupling rod 24a is slidable in a housing hole 24c formed in the center of the guide 22e. The separation distance between the cutting teeth head 30 and 3 housing hole 24c. The coupling spring 27 includes the variable length coupling rod 24a and the both ends are fixed to the cutting teeth head 30 and the guide 22e. In this mechanism, when external attraction force is applied to the cutting teeth head 30 attracted from the guide 22e then the coupling spring 27 stretch and the separation distance between the cutting teeth head 30 and the guide 22e increases. In other words, the venous valve incising cutter 204 regarding the fifth embodiment has the coupling rod, instead of the coupling rod 24 that a fixed length, includes a variable length coupling rod and a coil spring so that a gap between the cutting teeth head 30 and the guide 22e is stretchable against the elasticity of the coupling spring 27.

As far as the coupling spring 27 stretches within the elastic limit when an external force is applied by the finger tips to the cutting teeth head 30 and the guide 22e, either a dense wound coil spring or a rough wound coil spring can be used of the coupling spring 27.

Figure 12A:
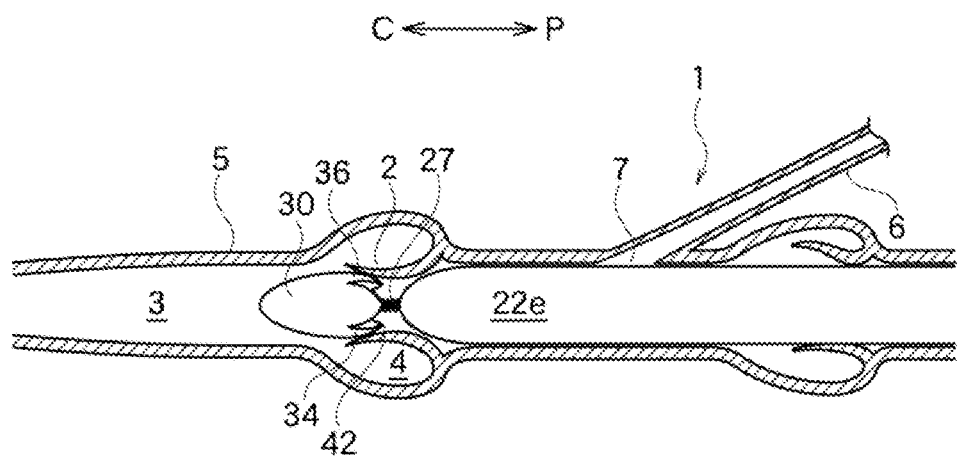
FIGS. 12A and 12B schematically illustrate the use of the venous valve incising cutter regarding the fifth embodiment. That is.
Figure 12B:
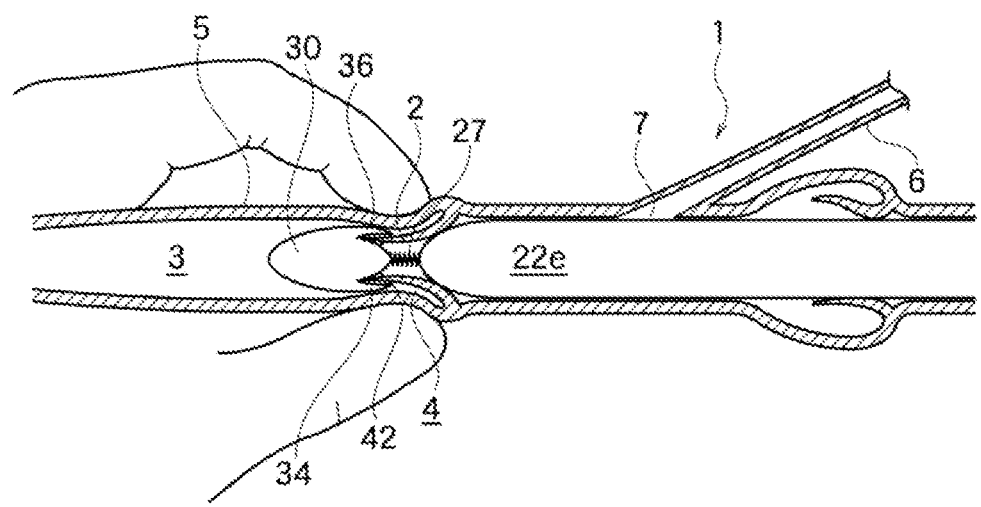

The second treatment method using the venous valve incising cutter 204 regarding the fifth embodiment is explained using FIGS. 12A and 12B.

Up to the state that the venous valve incising cutter 204 regarding the present invention is inserted so that the front end of the guide 22e reaches the center C side of the venous valve 2 locating most center C of the vein 1 after inserting into the lumen 3 of the vein 1, same Step 1 to Step 3 in the first treatment are executed.

In Step 4 of the second treatment method, the surgeon draws the wire 26 out from the vein after confirming that the front end of the guide 22e reaches the center C side of the venous valve 2 locating most center C of the vein 1. Then the surgeon can percept the cutting teeth head 30 sticks the venous valve 2 through tactile perception of finger tips when the venous valve 2 closes, as shown in FIG. 5C under assumption that the venous valve incising cutter 204 is used substitute for the venous valve incising cutter 20, at the constriction site where the radius of the venous valve incising cutter 204 is small because of the coupling area between the back end of the cutting teeth head 30 and the front end of the guide 22e.

On the other hand, even when the venous valve 2 does not closes, the surgeon percept the position of the venous valve 2 at the constriction site which is between the back end of the cutting teeth head 30 and the front end of the guide 22e.

The surgeon holds the position of the venous valve 2 with a strong pincer grasp. Then the gap between the cutting teeth head 30 and the guide 22e expands so that the venous valve 2 thrust into the gap.

Even after Step 4 of the second treatment method, Step 5 and Step 6 of the second treatment method are same as Step 5 and Step 6 of the first treatment method, respectively, except for using the venous valve incising cutter 204 instead of the venous valve incising cutter 20. The surgeon incises the venous valve 2 into three incised lines; two by two blade lines of the outer blades 40a and one by a blade line of the inner blade 40b. As the next proceeding, the surgeon draws the wire 26 to the position of the next venous valve 2 which usually locates several centimeters peripheral P side from the previous venous valve 2 already incised (Step 3 of the second treatment method). The surgeon repeats Step 4 and Step 5 of the second treatment method and confirms all of the venous valves 2 in the vein 1 to be grafted are incised.

A merit to use the venous valve incising cutter 204 is that the risk to damage vessel endothelium, irregular vessel wall or vascular bifurcation of the branching vessel in the vein 1 into which the venous valve incising cutter 203 is inserted can be minimized as less as possible by shortening the gap or the separation length between the cutting teeth head 30 and a guide 22e. If it is difficult for the surgeon to incise the venous valves by such shortening as shown in FIG. 12A, he/she can hold the position of the venous valve with a strong pincer grasp of his/her finger tips and then the gap between the cutting teeth head 30 and the guide 22e expands so that the venous valve 2 thrusts into the gap as shown in FIG. 12B. As the result, the surgeon can incise the venous valve without damaging other parts of vein 1 as expected. In the second treatment method, the surgeon can incise the venous valves 2 in a sequence of steps explained above after he/she inserts the venous valve incising cutter 204 into the vein 1. Therefore, by using the venous valve incising cutter 204 regarding the fifth embodiment, surgeons can safely and easily incise the venous valves 2 even if they have no sufficient experiences in vessel surgery.

The variable length coupling rod 24a has a stopper at the end of the rod which is formed in the extension of the insertion hole 24c drilled in the guide 22e. The stopper is out of the range shown in FIGS. 12A and 12B and not shown in the FIGS. 12A and 12B. The stopper limits the gap or the separation length between the cutting teeth head 30 and the guide 22e. Once the venous valve 2 is thrust in the gap between the cutting teeth head 30 and the guide 22e, the venous valve 2 does not come out from the constriction at the position of the gap since the gap, which is the gap or the separation length, is limited not to expand so much by drawing the wire 26.

For the venous valve incising cutter 204, the coupling spring 27 that makes the variable length coupling rod 24a stretchable between the cutting teeth head 30 and the guide 22e by a strong pincer grasp of the surgeon's finger tips includes the variable length coupling rod 24a and the both ends are fixed to the cutting teeth head 30 and the guide 22e. Other mechanisms, such as the coupling spring 27 is put inside the guide 22e and the stopper is fixed to the outside of the variable length coupling rod 24a so that the coupling spring 27 constantly pulls or pushes the variable length coupling rod 24a into the guide 22e at minimum of the stopper ceasing at the front end of the guide 22e and the cutting teeth head 30, may be adopted to make the separation distance, that is the gap, between the cutting teeth head 30 and the guide 22e variable. This construction has an effect that irrigation and sterilization of the venous valve incising cutter 204 are easily reliable since the coupling spring 27 of the venous valve incising cutter 204 does not expose outside.

The manufacturing method of the venous valve incising cutters 204 of the fifth embodiment is explained in the follow paragraphs.

The process 1 and the process 2 of the manufacturing method for the venous valve incising cutters 204 are same as the process 1 and process 2 of that for the venous valve incising cutters 20, respectively, except for using the variable length coupling rod 24a which is longer that the coupling rod 24.

In the process 3 of the manufacturing method for the venous valve incising cutters 204, the guide 22e is made by molding or rotation milling and a insertion hole 24c in the rotational axis in which a variable length coupling rod 24b is inserted (however, the end of the insertion hole 24c is not drilled out or opened at the opposing end against the cutting teeth head 30) is drilled in the guide 22e.

In the process 4 of the manufacturing method for the venous valve incising cutters 204, the variable length coupling rod 24a is inserted into the coupling spring 27 and the other end of the variable length coupling rod 24a is inserted into the insertion holed 24c which is drilled to the guide 22e. Then the coupling spring 27 is fixed to the cutting teeth head 30 and the guide 22e or screwed in to the inner threads formed in the back end of the cutting teeth head 30 and the front end of the guide 22e where the surface of the spring 27 works as a thread ridge. For the fixing of the coupling spring 27, welding is used but other connection methods may be adopted.

The cutting stabbers 34 formed in the posterior portion 32 of the cutting teeth head 30 or the outer blades 40a are not only the blades having knife-point 42 as shown in FIGS. 4A and 4B but also those having non-sharp tip incising blade 15a. as shown FIG. 7.

The cutting teeth head 30, the guides 22, 22d, 22e, 25d, the coupling rod 24, the variable length coupling rods 24a, the intra-guide coupling rod 25c, the wire 26, the coupling spring 27 are made of a metal. For the metal materials, a stainless steel equivalent to SUS304 is preferred, however other metals having properties of harmless to human tissues and heat resistance in the sterilization and plastic materials having harmless to human tissues and heat resistance in the sterilization are usable.

Since the venous valve incising cutters 20, 201, 202, 203 and 204 have more than four cutting stabbers 34 around the axis T in the posterior portion 32 of the cutting teeth head 30, any of the cutting stabbers can hit the venous valve with whatever angle the surgeon inserts any of these venous valve incising cutters against the vein 1. Therefore the surgeon can incise the venous valves by one inserting action of the venous valve incising cutters 20, 201, 202, 203 and 204 into the vein 1.

Since the venous valve incising cutters 20, 201, 202, 203 and 204 have more than four cutting stabbers 34, the outer surrounding surface 36 of a cutting stabbers 34 and the other out surfaces 36 of other cutting stabbers 34 prevent the vessel endothelium and vascular bifurcation 7 of the branching vessel 6 to come close to the apex 42 of the cutting stabber 34 in the radial plane of the venous valve incising cutters 20, 201, 202, 203 and 204 from outside thereof. Therefore, there is little possibility that the venous valve incising cutters 20, 201, 202, 203 and 204 damage the vessel endothelium and the branching vessel 6 and even the surgeons who have little experiences of the non-reverse and in-situ treatments for artery revascularization treatments can safely incise venous valves 2. By using these venous valve incising cutters 20, 201, 202, 203 and 204, patients are assured safe treatments.

Surgeons enable to incise the venous valves with a smooth cut wound using the venous valve incising cutters 20, 201, 202, 203 or 204 since they have the cutting stabbers 34 which have the outer blades 40a and the inner blades 40b both having sharp ridges.

The manufacturing method for the venous valve incising cutters 20, 201, 202, 203 and 204 enable to fabricate the cutting stabbers 34 in the posterior portion 32 of the cutting teeth head 30.

Since the surgeons who have little experiences of artery revascularization treatment can safely operate for such treatments using the venous valve incising cutter 20, 201, 202, 203 or 204, it can be expected to increase professional vascular surgeons who execute artery revascularization treatments experienced with the venous valve incising cutter 20, 201, 202, 203 or 204. The increase of such professional vascular surgeons results in saving more patients who suffer from ischemia-induced necrotic limbs, leg amputation etc.

In the above discussion, we have explained some of the embodiments of the present invention. The present invention is not limited within the embodiments as illustrated in the above explanations and drawings. Various modifications in the range of the same concept of the present invention and those which have combinations of plurality of the elements regarding the present invention in an appropriate method are included as a same or an equivalent invention thereto. Some of the elements in the above embodiments can be omitted from the implementation without departing from the scope of the present invention.

As such an example as a same or an equivalent invention, a venous valve incising cutter that has a cutting stabber composed of a curved surface which is a part of the outer surrounding surface of the cutting teeth head outside thereof and one or more than three planar surfaces inside thereof is included in the present invention.

The present application claims domestic priority to International Patent Application No. PCT/JP2014/052511, filed Feb. 4, 2014, and foreign priority to Japanese Patent Application No. 2015-008650, filed Jan. 20, 2015, each disclosure of which is incorporated herein by reference in its entirety for some embodiments of the present invention.

What is claimed is:

1. A venous valve incising cutter comprising:
   a cutting teeth head having a partly spheroid shape,
   a guide,
   a coupling rod that has a smaller diameter than the diameter of the guide, and that couples to the cutting teeth head, and
   a wire that is connected to the guide at the side opposite the cutting teeth head,
   wherein the cutting teeth head, the guide, the coupling rod, and the wire are all aligned in a common rotational axis thereof,
   wherein the cutting teeth head has a posterior portion facing the guide and a fore portion on a reverse side thereof, the posterior portion having at least four cutting stabbers that are partly composed of the outer surrounding surface thereof and are evenly distributed on the outer surrounding surface of the cutting teeth head, each of the cutting stabbers having a substantially triangular pyramid shape of an outer side is a part of the outer surrounding surface of the posterior portion of the cutting teeth head, the outer side curving in toward the guide at an apex of the pyramid shape, and the apex having an angle at a cross section of the vertical plane that intersects the apex and the common rotational axis that is large enough to incise a valve without severing the valve, and wherein the fore portion has a shape of a hemispheroid of which a major radius along the common rotational axis is larger than a maximum radius perpendicular to the common rotational axis, and the outer surrounding surface of the posterior portion of the cutting teeth head is consistent with a shape of a hemispheroid of which a major radius along the common rotational axis is smaller than that of the major radius along the common rotational axis of the hemispheroid of the fore portion, or a shape of a hemisphere of which radius perpendicular to the common rotational axis equals that of the maximum radius perpendicular to the common rotational axis of the cutting teeth head, or the outer surrounding surface of the cutting teeth head is consistent with an egg-shape.

2. The venous valve incising cutter according to claim 1, wherein the one side of each of the cutting stabbers that is a part of the outer surrounding surface of the posterior portion of the cutting teeth head is partly composed of a curved surface, and one or more of the other sides of each of the cutting stabbers are also curved.

3. The venous valve incising cutter according to claim 2, wherein the cutting teeth head has a cylindrical portion having a radius perpendicular to the common rotational axis equal to that of the maximum radius perpendicular to the common rotational axis, the cylindrical portion being between the fore portion and the posterior portion.

4. A manufacturing method for a venous valve incising cutter according to claim 2 including a first combination of a process to slit the posterior portion of the cutting teeth head up in a plane at a certain inclined angle from the outer surrounding surface of the posterior portion up to the rotational axis of the posterior portion and a process to repeat to do the same in every angle, that is the angle of 360 degrees divided by an number of pieces of the cutting blades and the other combination of a process to slit the posterior portion of the cutting teeth head up in a plane including a point to be the knife-pint of the cutting blade at the symmetrically same inclined angle from the outer surrounding surface of the posterior portion up to the rotational axis of the posterior portion and a process to repeat to do the same in every same angle as the first combination of the processes.

5. The venous valve incising cutter according to claim 1, wherein each of the cutting stabbers has a non-sharp tip shape.

6. The venous valve incising cutter according to claim 1, wherein each of the cutting stabbers has such a roughly triangular pyramid shape that the apex is a non-sharp tip shape.

7. The venous valve incising cutter according to claim 1, wherein each cutting stabber has a knife-point or a non-sharp tip incising edge which is in an inner range of the rotational surface radius of the cutting teeth head.

8. The venous valve incising cutter according to claim 1, wherein two ridge lines of each cutting stabber, which are edges made in the outer surrounding surface of the cutting teeth head, form curved lines like as sides of Reuleaux triangle.

9. The venous valve incising cutter according to claim 1, wherein the cutting stabbers continuously line the circumference of the cutting teeth head.

10. The venous valve incising cutter according to claim 1, wherein adjacent cutting stabbers have a common end point.

11. The venous valve incising cutter according to claim 1, wherein the guide comprises a main guide, one or more sub-guides and one or more intra-guide coupling rods coupling therebetween.

12. The venous valve incising cutter according to claim 1, wherein the coupling rod is a variable length coupling rod operable to adjust a distance between the cutting teeth head and the guide.

13. The venous valve incising cutter according to claim 1, wherein the coupling rod comprises a variable length coupling rod and a coupling spring configured so that a distance between the cutting teeth head and the guide is adjustable as the coupling spring is stretched against an elasticity of the coupling spring.

14. The venous valve incising cutter according to claim 1, wherein provided that the maximum radius perpendicular to the common rotational axis of the cutting teeth head is x, a shortest distance between the apex and the common rotational axis is y, the distance between the cutting teeth head and the guide is h, and a length of the posterior portion of the cutting teeth head along the common rotational axis is z, y/x is in a range of 1/3 to 1/2, z/2x is in a range of 0.8 to 1.3 and x/h is greater than 1.3.

15. A manufacturing method for a venous valve incising cutter according to claim 1 including:

a process to slit the posterior portion of the cutting teeth head up in a plane at an inclined angle to the rotational axis toward the diameter of the posterior portion and a process to repeat the process to do the same on every angle that is the angle of 360 degrees divided by an even number of pieces of the cutting blades.

16. A manufacturing method for a venous valve incising cutter according to claim 1 including further a process to cut the knifepoint and a vicinity thereof in a plane with an different inclined angle to the axis from the angle that a ridge line, being formed by crossing of the two planes formed in the reverse side of the outer surrounding surface of the cutting teeth head, has to the axis.

17. A treatment method for the venous valve incising cutter according to claim 1, the method comprising:

anastomosing a harvested vein to a central portion of an artery at an upper part from an occluded part thereof, inserting the venous valve incising cutter into a lumen of the vein until a fore portion of the guide reaches the center side of a venous valve of the vein, pulling the wire outwardly after confirming the fore portion of the guide has reached the center side of the venous valve, pulling the wire so that the cutting blades incise the venous valve.

18. The venous valve incising cutter according to claim 1, wherein the angle at the cross section of the vertical plane that intersects the apex and the common rotational axis is between 53.0 and 60.5 degrees.

\* \* \* \* \*